United States Patent
Kil et al.

(10) Patent No.: US 9,474,970 B2
(45) Date of Patent: Oct. 25, 2016

(54) SYSTEM AND METHOD FOR PROCESSING MOTION-RELATED SENSOR DATA WITH SOCIAL MIND-BODY GAMES FOR HEALTH APPLICATION

(71) Applicants: David H. Kil, Santa Clara, CA (US); Bongjoo Shin, Santa Clara, CA (US)

(72) Inventors: David H. Kil, Santa Clara, CA (US); Bongjoo Shin, Santa Clara, CA (US)

(*) Notice: Subject to any disclaimer, the term of this patent is extended or adjusted under 35 U.S.C. 154(b) by 614 days.

(21) Appl. No.: 13/752,373

(22) Filed: Jan. 28, 2013

(65) Prior Publication Data

US 2013/0203475 A1    Aug. 8, 2013

Related U.S. Application Data

(60) Provisional application No. 61/591,084, filed on Jan. 26, 2012, provisional application No. 61/591,100, filed on Jan. 26, 2012, provisional application No. 61/619,145, filed on Apr. 2, 2012, provisional application No. 61/648,431, filed on May 17, 2012.

(51) Int. Cl.

| | |
|---|---|
| *A63F 9/24* | (2006.01) |
| *A63F 13/00* | (2014.01) |
| *A63F 13/428* | (2014.01) |
| *A63F 13/212* | (2014.01) |

(Continued)

(52) U.S. Cl.
CPC ............ *A63F 13/428* (2014.09); *A61B 5/1118* (2013.01); *A61B 5/1123* (2013.01); *A63F 13/00* (2013.01); *A63F 13/21* (2014.09); *A63F 13/212* (2014.09); *A63F 13/44* (2014.09); *A63F 13/65* (2014.09); *G06Q 10/101* (2013.01); *G06Q 50/01* (2013.01); *G09B 19/003* (2013.01); *A63F 13/92* (2014.09)

(58) Field of Classification Search
CPC ........ A63F 13/00; A63F 13/02; A63F 13/06; A63F 13/20; A63F 13/21; A63F 13/211; A63F 13/212; A63F 13/217; A63F 13/22; A63F 13/23; A63F 13/235; A63F 13/24; A63F 13/245; A63F 13/40; A63F 13/42; A63F 13/44; A63F 13/45; A63F 13/816; A63F 13/87; A63F 2300/10; A63F 2300/1006; A63F 2300/1012; A63F 2300/1018; A63F 2300/1037; A63F 2300/105; A63F 2300/1062; A63F 2300/6045; A63F 2300/63; A63F 2300/638; A63F 2300/8005; A63F 2300/8094; A61B 5/1118; A61B 5/1123; G09B 19/003; G09B 19/0038; G06Q 10/101; G06Q 50/01

See application file for complete search history.

(56) References Cited

U.S. PATENT DOCUMENTS

| | | |
|---|---|---|
| 6,210,272 B1 | 4/2001 | Brown |
| 6,582,380 B2 | 6/2003 | Kazlausky et al. |

(Continued)

OTHER PUBLICATIONS

Bonomi, A.G. et al.; "Improving assessment of daily energy expenditure by identifying types of physical activity with a single accelerometer"; Journal of Applied physiology, Sep. 2009, vol. 107, No. 3; p. 655-661.

(Continued)

*Primary Examiner* — Milap Shah
(74) *Attorney, Agent, or Firm* — Wilson & Ham

(57) ABSTRACT

A system and method for processing motion-related sensor data for health application examines motion-related signal from a motion sensor located on a subject on a frame-by-frame basis to detect physical activities performed by the subject. For each frame, a detected activity is classified into a category of activities and performance parameters of the detected activity are estimated.

18 Claims, 24 Drawing Sheets

(51) Int. Cl.

| | |
|---|---|
| A63F 13/65 | (2014.01) |
| A63F 13/44 | (2014.01) |
| A63F 13/21 | (2014.01) |
| G06Q 10/10 | (2012.01) |
| G06Q 50/00 | (2012.01) |
| G09B 19/00 | (2006.01) |
| A61B 5/11 | (2006.01) |
| A63F 13/92 | (2014.01) |

(56) References Cited

U.S. PATENT DOCUMENTS

| | | | |
|---|---|---|---|
| 7,141,026 B2 | 11/2006 | Arminian et al. | |
| 7,421,369 B2 | 9/2008 | Clarkson | |
| 7,450,002 B2 | 11/2008 | Choi et al. | |
| 7,647,196 B2 | 1/2010 | Kahn et al. | |
| 7,653,508 B1 | 1/2010 | Kahn et al. | |
| 7,668,691 B2 | 2/2010 | Counts et al. | |
| 7,695,406 B2 | 4/2010 | Waters | |
| 7,702,608 B1* | 4/2010 | Bererton et al. | 706/46 |
| 7,753,861 B1 | 7/2010 | Kahn et al. | |
| 7,837,595 B2 | 11/2010 | Rice | |
| 7,987,070 B2 | 7/2011 | Kahn et al. | |
| 8,055,720 B2 | 11/2011 | He et al. | |
| 8,113,991 B2* | 2/2012 | Kutliroff | A63B 71/0622 348/77 |
| 8,267,694 B1 | 9/2012 | Lamka | |
| 8,317,623 B1* | 11/2012 | Murphy et al. | 463/42 |
| 8,597,093 B2* | 12/2013 | Engelberg et al. | 463/1 |
| 9,223,855 B1* | 12/2015 | Wagner | G06F 17/30705 |
| 2005/0181347 A1* | 8/2005 | Barnes et al. | 434/350 |
| 2006/0018516 A1* | 1/2006 | Masoud | G06K 9/00342 382/115 |
| 2006/0141431 A1* | 6/2006 | Lee | 434/236 |
| 2008/0146334 A1* | 6/2008 | Kil | 463/36 |
| 2008/0176655 A1* | 7/2008 | James et al. | 463/42 |
| 2008/0262786 A1* | 10/2008 | Pavlidis | 702/141 |
| 2008/0318678 A1* | 12/2008 | Stivoric et al. | 463/36 |
| 2009/0048070 A1* | 2/2009 | Vincent | A63B 24/0021 482/8 |
| 2009/0118100 A1* | 5/2009 | Oliver | A63B 24/0062 482/8 |
| 2009/0210078 A1* | 8/2009 | Crowley | G06Q 30/02 700/91 |
| 2010/0125026 A1* | 5/2010 | Zavadsky | A63B 21/00 482/5 |
| 2010/0167801 A1* | 7/2010 | Karkanias et al. | 463/7 |
| 2010/0323794 A1* | 12/2010 | Su | 463/36 |
| 2010/0331146 A1* | 12/2010 | Kil | 482/8 |
| 2011/0046519 A1 | 2/2011 | Raheman | |
| 2011/0195780 A1* | 8/2011 | Lu | 463/31 |
| 2012/0029666 A1* | 2/2012 | Crowley | A63B 24/0062 700/91 |
| 2012/0041767 A1* | 2/2012 | Hoffman et al. | 705/1.1 |
| 2012/0042070 A1* | 2/2012 | Napolitano et al. | 709/224 |
| 2012/0215328 A1* | 8/2012 | Schmelzer | G06F 19/3481 700/91 |
| 2012/0237905 A1 | 9/2012 | Northcutt | |
| 2012/0253489 A1 | 10/2012 | Dugan | |
| 2013/0040714 A1* | 2/2013 | Rosing | 463/7 |
| 2014/0074265 A1* | 3/2014 | Arginsky | A63B 71/0622 700/91 |
| 2014/0100464 A1* | 4/2014 | Kaleal | A61B 5/0205 600/508 |
| 2015/0005911 A1* | 1/2015 | Lake, II | G06Q 50/22 700/91 |
| 2015/0050972 A1* | 2/2015 | Sarrafzadeh et al. | 463/7 |

OTHER PUBLICATIONS

Schmidt, Michael D. et al.; "Estimating Physical Activity Using the CSA Accelerometer and a Physical Activity Log", Sep. 2003, Med. Sci. Sports Exerc., vol. 35, No. 9; p. 1605-1611.

Mannini, Andrea et al.; "Machine Learning Methods for Classifying Human Physical Activity from On-Body Accelerometers"; Feb. 1, 2010, Sensors 2010, 10, p. 1154-1175; doi:10:3390/s100201154.

Yang, Che-Chang et al.; "A Review of Accelerometry-Based Wearable Motion Detectors for Physical Activity Monitoring"; Aug. 20, 2010; Sensors 2010, 10, p. 7772-7788; doi:10.3390/s100807772.

International Search Report and Written Opinion, PCT/US2013/023513.

Daniyalzade, et al., "Facebook Friend Suggestion", Retrieved at http://www.stanford.edu/class/cs229/proj2007/DaniyalzadeLipusFacebookFriendSuggestion.pdf, pp. 5, 2007.

Beshears, et al., "The Effect of Providing Peer Information on Retirement Savings Decisions," NBER working paper 17345, Aug. 2011.

Owens, T.; "How Much Weight Can the Average Man Lift?"; http://www.livestrong.com/article/395390theaverageweightamancanlift/; accessed Dec. 4, 2011.

Singleton, B.; "Calories Burned Through Strength Training"; http://www.livestrong.com/article/214892caloriesburned-duringresistancetraining/; accessed Dec. 4, 2011.

Maximum Heart Rate; Brianmac, http://www.brianmac.co.uk/maxhr.htm, accessed Dec. 9, 2011.

Gellish, R.L. et al., "Longitudinal Modeling of the Relationship between Age and Maximal Heart Rate," Medicine & Science in Sports & Exercise, 39 (5), p. 822829, 2007.

N. Christakis and J. Fowler, "The Spread of Obesity in a Large Social Network over 32 Years," The NEJM, 257: 370-379, 2007.

Kil and Piniewski, "PeaceHealth Trial Outcomes," PeaceHealth internal presentation, Nov. 2011.

Joey C. Eisenmann, Kelly R. Laurson, Katrina D. Dubose, Bryan K. Smith and Joseph E. Donnelly, "Construct validity of a continuous metabolic syndrome score in children," Diabetology & Metabolic Syndrome 2010, 2 :8 (Jan. 28, 2010).

E.M. Tapia, "Using Machine Learning for Realtime Activity Recognition and Estimation of Energy Expenditure," Ph.D. Dissertation, MIT, 2008.

D.T. Huynh, "Human Activity Recognition with Wearable Sensors," Ph.D. dissertation, Technische Universitat Darmstadt, Aug. 2008.

Mannini and A.M. Sabatini, "Machine Learning Methods for Classifying Activity from OnBody Accelerometers," Sensors 2010, 10, 1154-1175.

Robinson, A.; "How Many Calories Are Burned During 30 Minutes of Weight Lifting?"; Livestrong, http://www.livestrong.com/article/73356calculatecaloriesburnedcycling/, accessed Nov. 2011.

American Thoracic Society; "ATS Statement: Guidelines for the Six-Minute Walk Test"; http://www.thoracic.org/statements/resources/pfet/sixminute.pdf, accessed Nov. 2011.

Paap E, van der Net J, Helders PJM, Takken T. Physiologic response of the sixminute walk test in children with juvenile idiopathic arthritis. Arth Care Res 2005; 53:351356.

Ekodemos; "Cardiorespiratory Fitness Test"; http://www.ekodemos.se/cardiofitnesstest.pdf, accessed Nov. 2011.

T. Baranowski, et al., "Impact of an Active Video Game on Healthy Children's Physical Activity," Pediatrics, vol. 129, No. 5, Mar. 2012.

N. Yee, N. Ducheneaut, L. Nelson, and P. Likarish, "Introverted Elves & Conscientious Gnomes: The Expression of Personality in World of Warcraft," CHI, Vancouver, Canada, May 2011.

N. Ducheneaut, et al., "The Life and Death of Online Gaming Communities: A Look at Guilds in World of Warcraft," CHI, San Jose, CA, 2007.

Mindbloom.com, accessed in Nov. 2011.

Gomes, N., et al. "Steptacular: an incentive mechanism for promoting wellness"; Dec. 2011.

BrainResource.com, accessed in Sep. 2011.

Lumosity.com, accessed in Oct. 2011.

P. M. Kato, "Video Games in Health Care: Closing the Gap," Review of General Psychology, vol. 14, No. 2, pp. 113-121, 2010.

Polyvore.com, accessed in Nov. 2011.

Terrapass carbon footprint calculator, http://www.terrapass.com/carbon-footprint-calculator/, accessed Dec. 5, 2011.

S. M. Roth, "Perspectives on the future use of genomics in exercise prescription," J. Applied Physiology, vol. 104, pp. 1243-1245, 2008.

J.A. Babraj, et al., "Extremely short duration high intensity interval training substantially improves insulin action in young healthy males," BMC Endocrine Disorders, Jan. 2009.

(56) References Cited

OTHER PUBLICATIONS

J.L. Talanian, et al., Two weeks of highintensity aerobic interval training increases the capacity for fax oxidation during exercise in women, J. Applied Physiology, Dec. 2006.

J.P. Little, et al., "A practical model of low-volume high-intensity interval training induces mitochondrial biogenesis in human skeletal muscle: potential mechanisms," J. Physiology, Mar. 2010.

* cited by examiner

SYSTEM AND METHOD FOR PROCESSING MOTION-RELATED SENSOR DATA WITH SOCIAL MIND-BODY GAMES FOR HEALTH APPLICATION

CROSS REFERENCE TO RELATED APPLICATION

This application is entitled to the benefit of U.S. Provisional Patent Application Ser. No. 61/591,084, filed on Jan. 26, 2012, U.S. Provisional Patent Application Ser. No. 61/591,100, filed on Jan. 26, 2012, U.S. Provisional Patent Application Ser. No. 61/619,145, filed on Apr. 2, 2012, and U.S. Provisional Patent Application Ser. No. 61/648,431, filed on May 17, 2012, the disclosures of which are incorporated herein by reference.

BACKGROUND OF THE INVENTION

Most people understand the health benefits of exercising, such as walking or jogging, but do not find exercising fun. In addition, many people do not have the time to engage in low-intensity activity exercises, such as walking. For example, the traditional mantra of "10K steps a day" is impractical for most people as walking 10K steps would require two to four hours in a single day. Furthermore, such a monotonous, low-intensity activity can result in (1) boredom, which leads to high dropout, (2) inefficient fitness benefit given time investment for busy professionals, and/or (3) potential injuries and deteriorating flexibility associated with endurance running.

In order to address these issues, activity monitoring devices with supporting fitness programs have been developed. However, current fitness programs that use activity monitoring devices do not adequately provide the desired results for their users. Thus, there is a need for a health system and method based on one or more activity monitoring devices that can reduce dropout rate, increase fitness benefit and/or reduce potential injuries or deterioration of flexibility.

SUMMARY OF THE INVENTION

A system and method for processing motion-related sensor data for health application examines motion-related signal from a motion sensor located on a subject on a frame-by-frame basis to detect physical activities performed by the subject. For each frame, a detected activity is classified into a category of activities and performance parameters of the detected activity are estimated.

In an embodiment, a method for processing motion-related sensor data for health application comprises receiving motion-related signal from a motion sensor located on a subject, examining the received motion-related signal on a frame-by-frame basis to detect physical activities performed by the subject, each frame representing a predefined time interval, for each frame, classifying a detected activity into a category of activities, and for each frame, estimating performance parameters of the detected activity.

In an embodiment, a system for processing motion-related sensor data for health application comprises a digital signal processing unit, a frame-based activity classification unit and a parameter estimation unit. The digital signal processing unit is configured to receive motion-related signal from a motion sensor located on a subject and to examine the received motion-related signal on a frame-by-frame basis to detect physical activities performed by the subject. Each frame represents a predefined time interval. The frame-based activity classification unit is configured to classify, for each frame, a detected activity into a category of activities. The parameter estimation unit is configured to estimate, for each frame, performance parameters of the detected activity.

Other aspects and advantages of the present invention will become apparent from the following detailed description, taken in conjunction with the accompanying drawings, illustrated by way of example of the principles of the invention.

DETAILED DESCRIPTION

Figure 1:
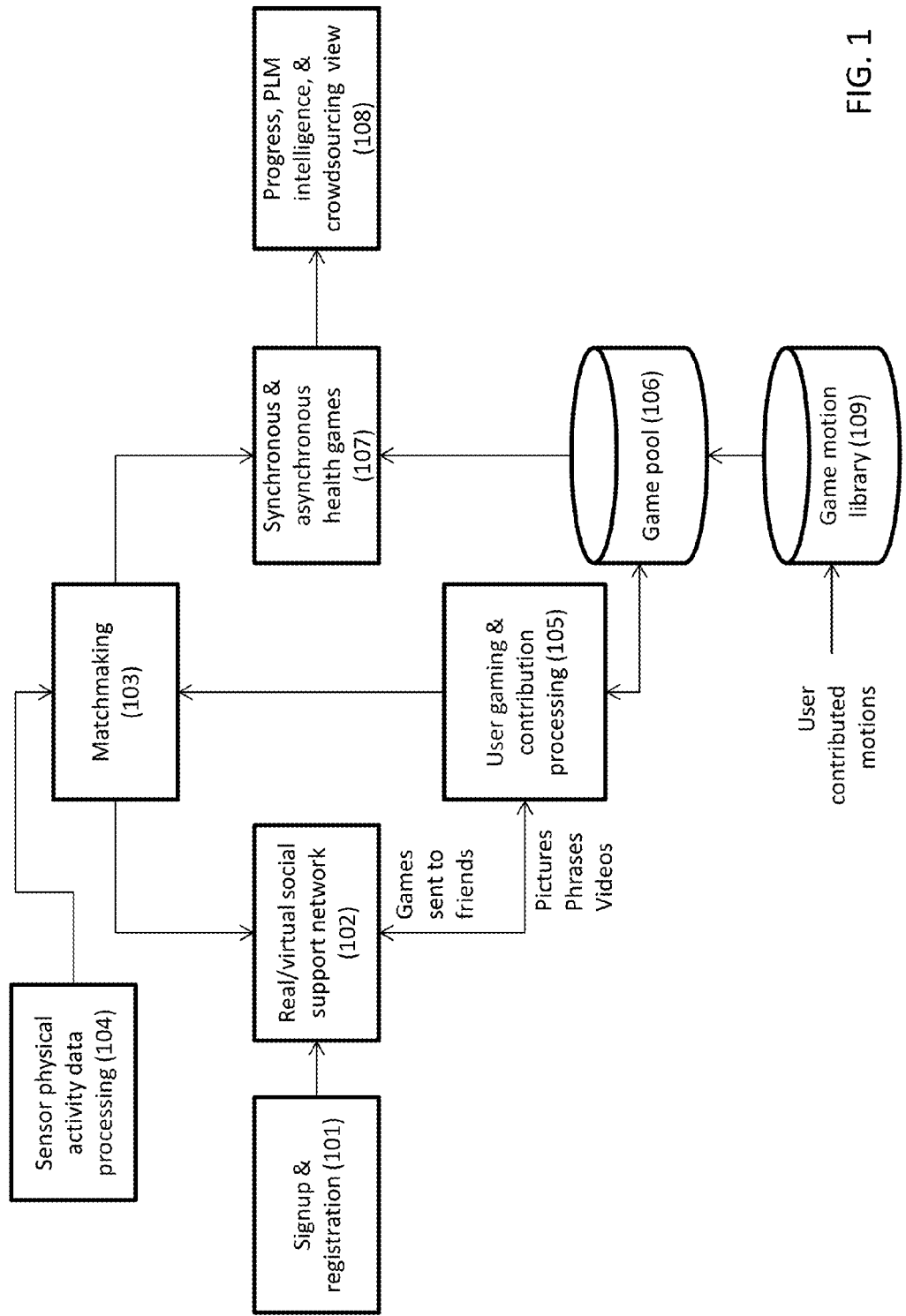
FIG. 1 is a high-level flowchart of using a fitness game application in accordance with an embodiment of the invention of a system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

Various embodiments of the invention described herein relate to a system and method to encourage users to exercise in a stimulating manner using electronic activity monitoring devices. Activity monitoring in terms of steps or distance has been around for a long time. Systems for activity monitoring using chest straps, eyewear, and accelerometers have been developed. Unfortunately, such activity monitoring is one dimensional and insufficient in modeling a complex human fitness state. Any feedback system based on steps is not rich enough to engage users and, more importantly, will fail to provide right performance metrics that can lead to improved health outcomes over time.

In addition, activity classification using multiple sensors, such as cameras, Global Positioning Systems (GPSs) and wearable sensors, has been an area of active research. An activity classification system using routes estimated from GPS has been described in literature. A system for monitoring sedentary sitting, walking/running, and falling has also been described in literature. Various techniques for recognizing physical activities have also been described in literature. One technique uses a hidden Markov model with Viterbi algorithm to recognize activities based on measurements from inertial sensors. Other techniques have focused on activity classification using multiple on-body devices. However, it is unrealistic to assume that people would wear multiple devices on multiple body locations for activity classification.

As a result, the current crop of health and fitness solutions with sensors focuses on steps. Strava is targeting cycling enthusiasts with GPS. Typical sensors used for measurement are either GPS or accelerometer with or without an altimeter. Nike and Jawbone offer a social dimension through competitions, usually based on distance or speed over distance. A few companies, such as Keas and Fitocracy, have introduced self-reported fitness games based on points and competitions without sensor validation.

Recently the idea of linking games and physical activities has emerged. An apparatus has been described in literature where a smartphone is used to track user information and to provide pre-emptive warnings using an avatar when the user is engaged in undesirable behaviors. In addition, a board game has been proposed, which incorporates various healthy lifestyle learning lessons including exercise and quiz. A system to educate children about healthy lifestyle by tying prizes to winning competitions has been developed.

Unfortunately such games and fitness applications do not engage consumers in the long run. Most games and applications experience dropout rates of over 90% in a few months. Furthermore, these games and applications do not answer the important so-what question in terms of causal relationships between lifestyle and health-progress metrics linked to health outcomes and medical costs that consumers and businesses care about.

The benefits of short-duration interval training have been well documented in medical journals. Even then, interval training focusing on cardio alone, while better than endurance running, can lead to burnouts and injuries. Therefore, what is needed is an engaging gaming platform that encourages people to perform a balanced set of short-duration motions with proper rest during which fat burning takes place in a relaxed setting. Such motion regiment helps people improve their balance, flexibility, strength, cardio, and body composition in a natural sequence, aided by multidimensional progress tracking and social reinforcement. These motions and games must be tailored to the target population to maximize the probabilities of user engagement and improved health outcomes. Furthermore, the game environment must offer a sense of caring, being together, and mind-body nurturing by combining physical activities with brain/emotion exercise and relaxation in a single game.

An embodiment of the invention includes a fitness game application that can be played on smartphones, tablets, computers or any device with a display screen and a processor, e.g., a central processing unit (CPU). FIG. 1 shows a high-level flowchart of using the fitness game application in accordance with an embodiment of the invention. This process begins at block 101, where a user executes a signup and registration operation. The signup and registration operation may involve the user entering user information in the fitness game application or an appropriate website. After the signup and registration operation has been completed, the user is assigned to a virtual network of game players based on the user profile. As the user plays games on the fitness game application alone, in competition, or in collaboration using points accumulated by performing motions, a real/virtual social support network can be provided, at block 102, using real friends recommended by a matchmaking operation performed by a matchmaking engine, at block 103. In an embodiment, the matchmaking engine is a software program that looks for a player's playing patterns as well as fitness metrics and motion preferences to match him or her to the right users who are likely to enjoy playing together. The matchmaking engine would typically reside in one or more servers that provide support for the fitness game application running on various user devices. The user can also invite his or her real friends and family members to join, thereby creating a close-knit social support network.

At block 104, physical activity data from one or more motion sensors associated with the fitness game application is processed by a sensor physical activity data processing engine. In an embodiment, the sensor physical activity data processing engine is a software program that recognizes user motions being performed, estimates motion performance parameters, and assigns points, which the user can use to play games. The sensor physical activity data processing engine may reside in any computing device, e.g., a smartphone of the user.

At block 105, user gaming information and user contributions are processed by a user gaming and contribution processing engine. The user can contribute data to a health game pool 106, which can be stored in any computer storage medium, in a number of ways. The user can create and upload pictures, digital paintings (created as part of a game), phrases, poems, or videos and specify that they be delivered to his friends and/or family members. The user can also specify motion categories that will populate a game page based on the knowledge of his friends' fitness state and workout preferences or let the system assign motions based on its assessment of the recipient's fitness state and preferences. The user can also upload his favorite motions to be shared with his social network and others. In an embodiment, the user gaming and contribution processing engine is a software program that converts user-contributed content into tailored games, which get delivered to the recipients, while studying user gaming playing patterns to improve matchmaking.

The games can be played synchronously or asynchronously, at block 107. In an embodiment, family members can take turns or play together while virtual friends can play games asynchronously. At block 108, a stakeholder view facilitates information visualization of the user's playing patterns, progresses made by similar cohorts, i.e., people like me (PLM), and how crowdsourcing is used to motivate the user. Gaming motions stored in a motion library 109, which can be stored in any computer storage medium, can be assigned to the games or the user can perform them independent of the games to earn points with which they can play the games separately during motion interval training.

During the synchronous or asynchronous gaming phase, the user performs prescribed motions and earns points upon validation by sensor data processing algorithms. The user then uses these points to solve a puzzle, improve mood by shooting down unhappy faces raining down, enhance spatial reasoning skills by unscrambling scrambled pictures, and buy tools to accomplish a feat, such as, but not limited to painting, composing a poem, etc. Further, the user can play board games to win prizes. When the user exhausts the points, then the user can do more motions either as part of games or separately by going to the motion playlist page of the fitness game application.

Finally, the backend analytics engine processes game and sensor data to track and report on the user's health and fitness progress. Furthermore, profile and game based segmentation facilitates performance-comparison reporting on the user's progress in relation to his cohorts (people-like-me (PLM) intelligence). The crowdsourcing intelligence view promotes players to receive and provide social nudging by publishing their creations and accomplishments while voting on others' creations and accomplishments as part of mutual social nudging.

Figure 2:
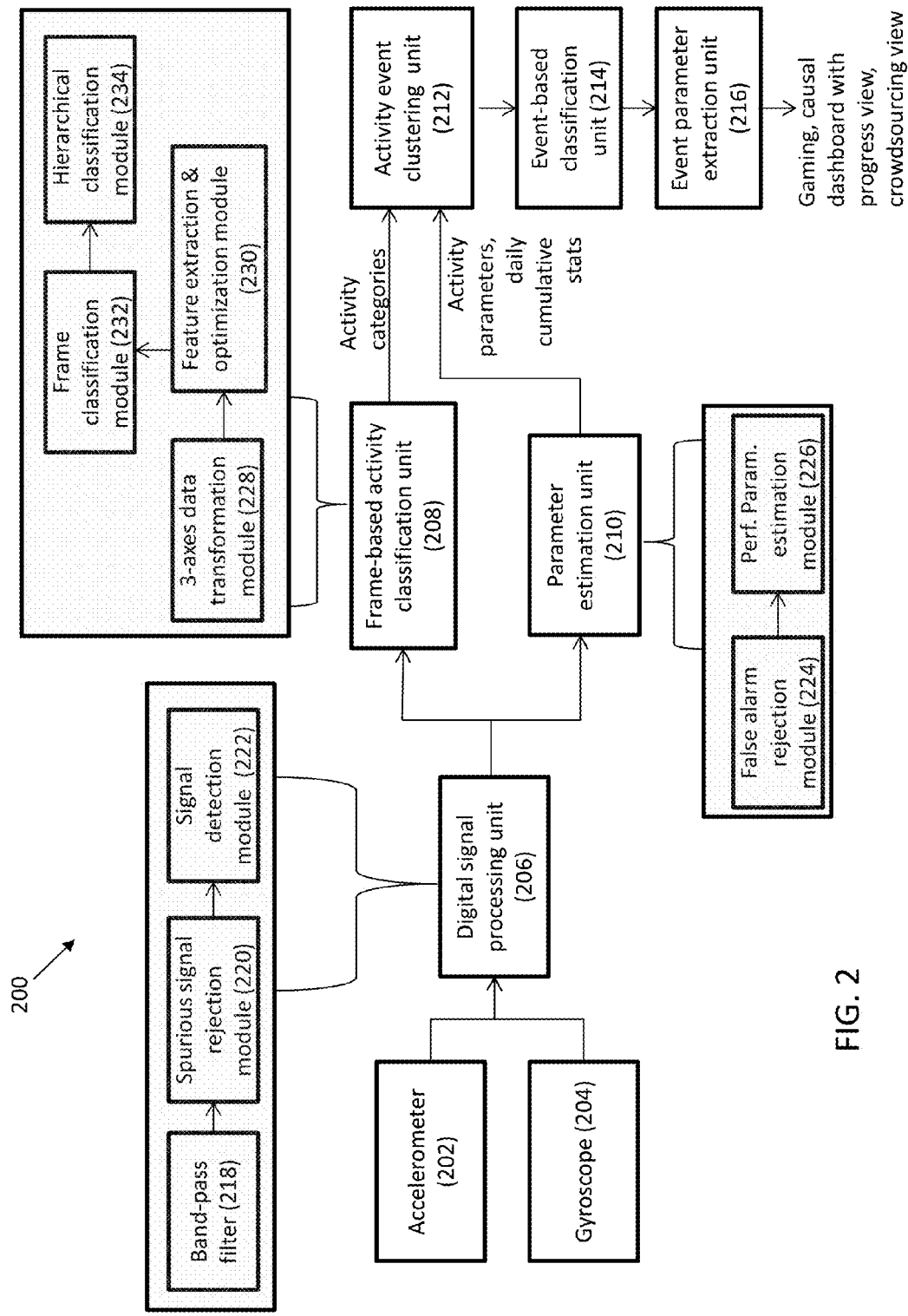
FIG. 2 is a block diagram of a sensor physical activity data processing engine in accordance with an embodiment of the invention.

Turning now to FIG. 2, a block diagram of a sensor physical activity data processing engine 200 in accordance with an embodiment of the invention is shown. The sensor physical activity data processing engine is configured to receive sensor physical activity data from one or more sensors, such as, but not limited to, an accelerometer 202 and a gyroscope 204. One or more of these sensors may be part of a computing device on which the fitness game application is running or may be a stand-alone peripheral device that can be connected via a wireless or wired connection to the computing device. As shown in FIG. 2, the sensor physical activity data processing engine includes a digital signal processing unit 206, a frame-based activity classification unit 208, a parameter estimation unit 210, an activity event clustering unit 212, an event-based classification unit 214 and an event parameter extraction unit 216.

The digital signal processing unit 206 is configured to receive and process the sensor physical activity data from one or more sensors, e.g., the accelerometer 200 and the gyroscope 202, in the form of electrical signals. The digital signal processing unit includes a band-pass filter 218, a spurious signal rejection module 220 and a signal detection module 222. The band-pass filter filters the received sensor physical activity signal to improve signal-to-noise ratio. The spurious signal rejection module eliminates spurious noise in the received signal. Spurious noise can occur when the user drops a sensor or the computing device with the sensor(s) or hits an object with it. The signal detection module analyzes the resulting signal and looks for the presence of activities in the signal based on energy and regularity over a certain time frame $T_f$.

The parameter estimation unit 210 estimates activity parameters using the detected activities in the received signal. The activity parameter estimation is performed for the same time frame $T_f$ instead of computing real-time step count as most pedometers do. The main reason for using the time frame $T_f$ is for the rejection of false alarms that can occur while riding a bus/train, driving a car on bumpy roads, or even riding an elevator that makes jerky stops on floors. The parameter estimation unit includes a false-alarm rejection module 224 and a performance parameter estimation module 226. The false-alarm rejection module scans every frame of the received signal to check for the consistency of detected movements. After removing false alarms on a frame-by-frame basis, the performance parameter estimation module estimates physical activity performance parameters, such as counts for each frame, range of motion for each frame, balance score for each frame, steps/strides per frame or revolution per frame, which will be rolled up to the final sampling rate for output generation. The performance parameter estimation module uses a bank of matched filters for the frame-based parameter estimation, where each filter is optimized for each sensor and each motion category.

The frame-based activity classification unit 208 is configured to perform frame-based activity classification in parallel to the performance parameter estimation preformed by the parameter estimation unit 210. The frame-based activity classification unit includes a three-axis data transformation module 228, a feature extraction and optimization module 230, a frame classification module 232 and a hierarchical classification module 234. The three-axis transformation module transforms three-axis data from the sensor(s) to multiple projection spaces encompassing, but not limited to, a spectral domain, time-frequency distribution, raw channel and magnitude correlation space, nonlinear time-embedded space, and band-pass filter outputs. The feature extraction and optimization module 232 extracts features from the multiple projection spaces for activity classification.

Figure 3:
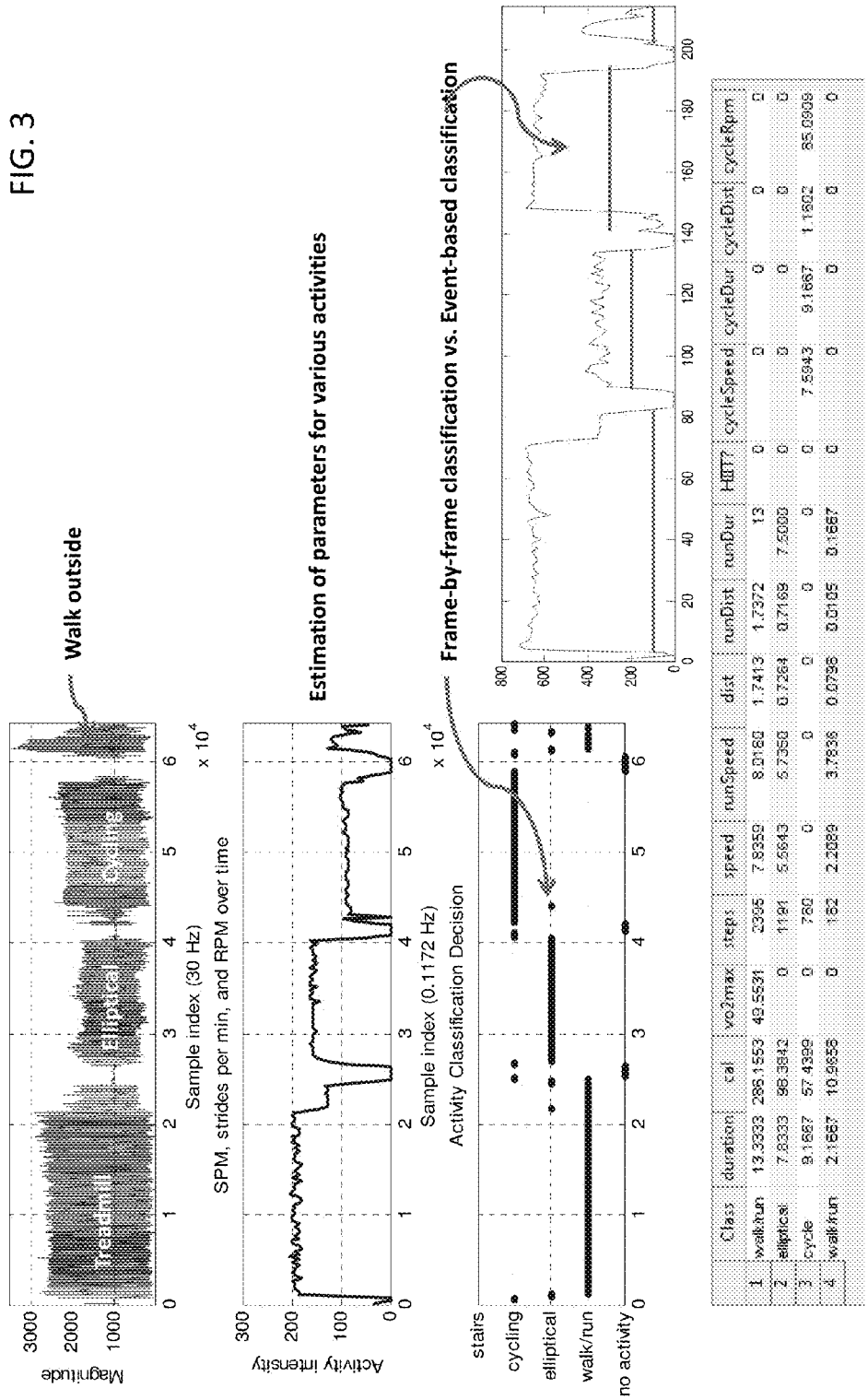
FIG. 3 shows frame-by-frame classification decisions for three major activity categories, such as walk/run, elliptical, and cycling, in accordance with an embodiment of the invention.
Figure 4:
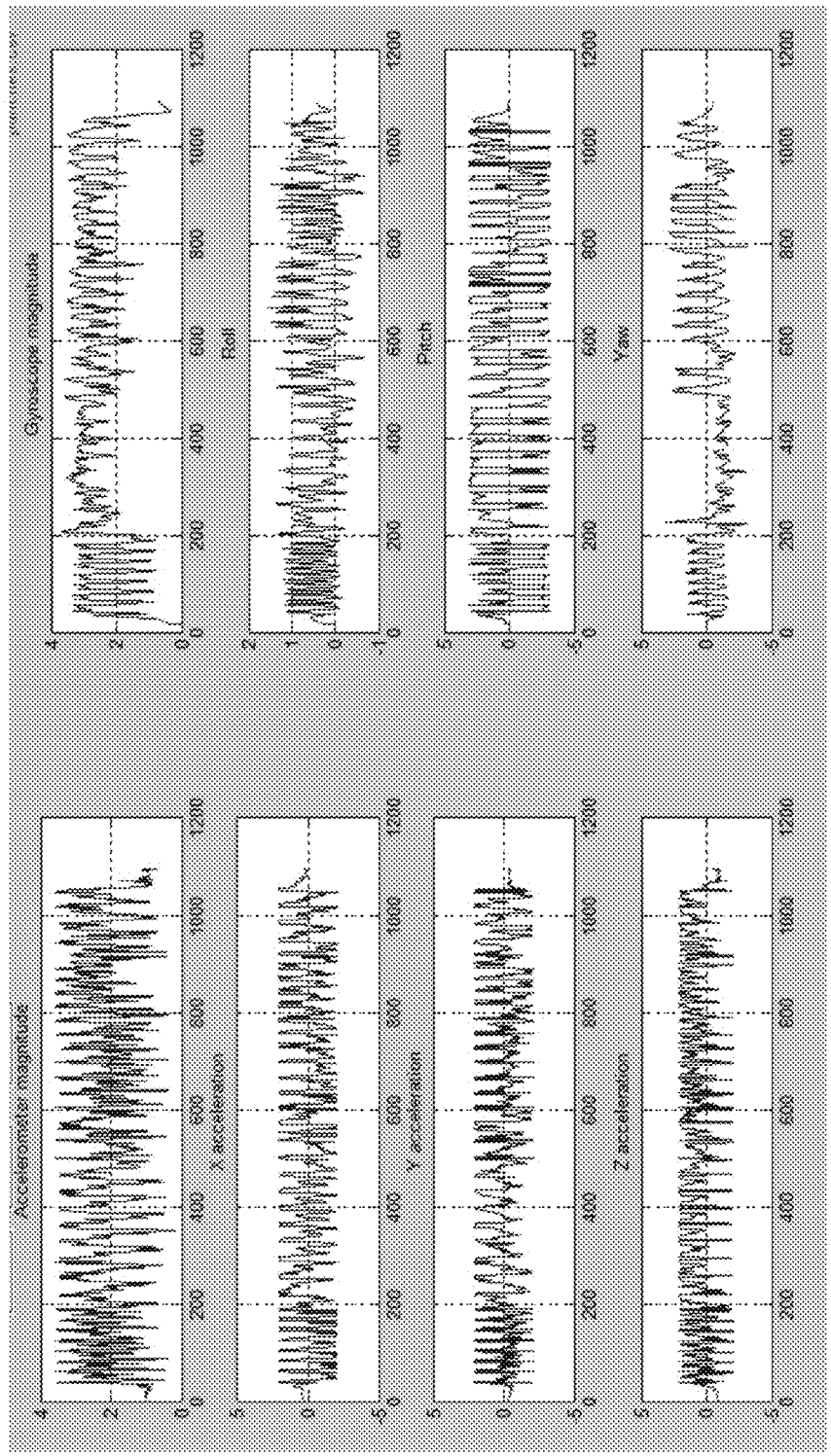
FIGS. 4-11 show typical motion signatures captured through sensor signal processing and classification or recognition in accordance with an embodiment of the invention.
Figure 5:
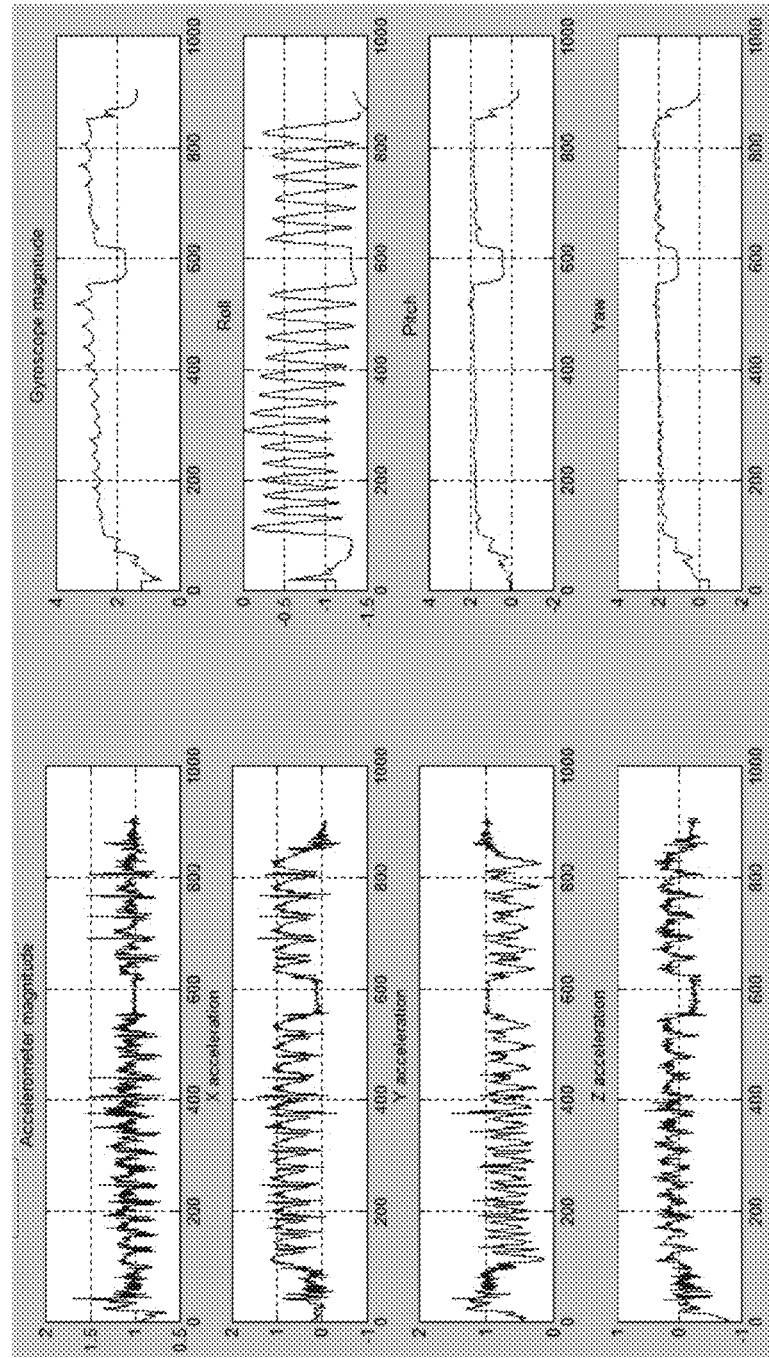
Figure 6:
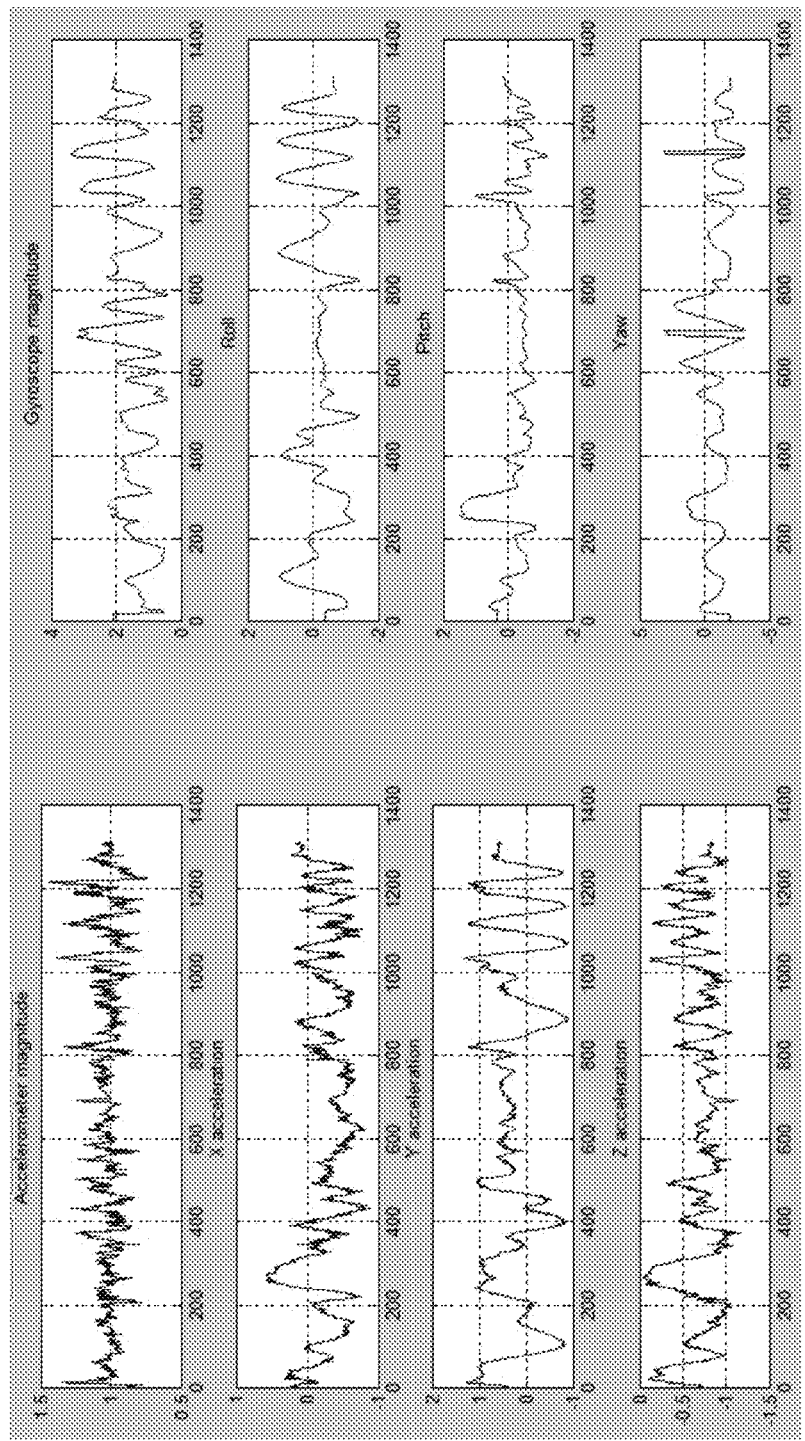
Figure 7:
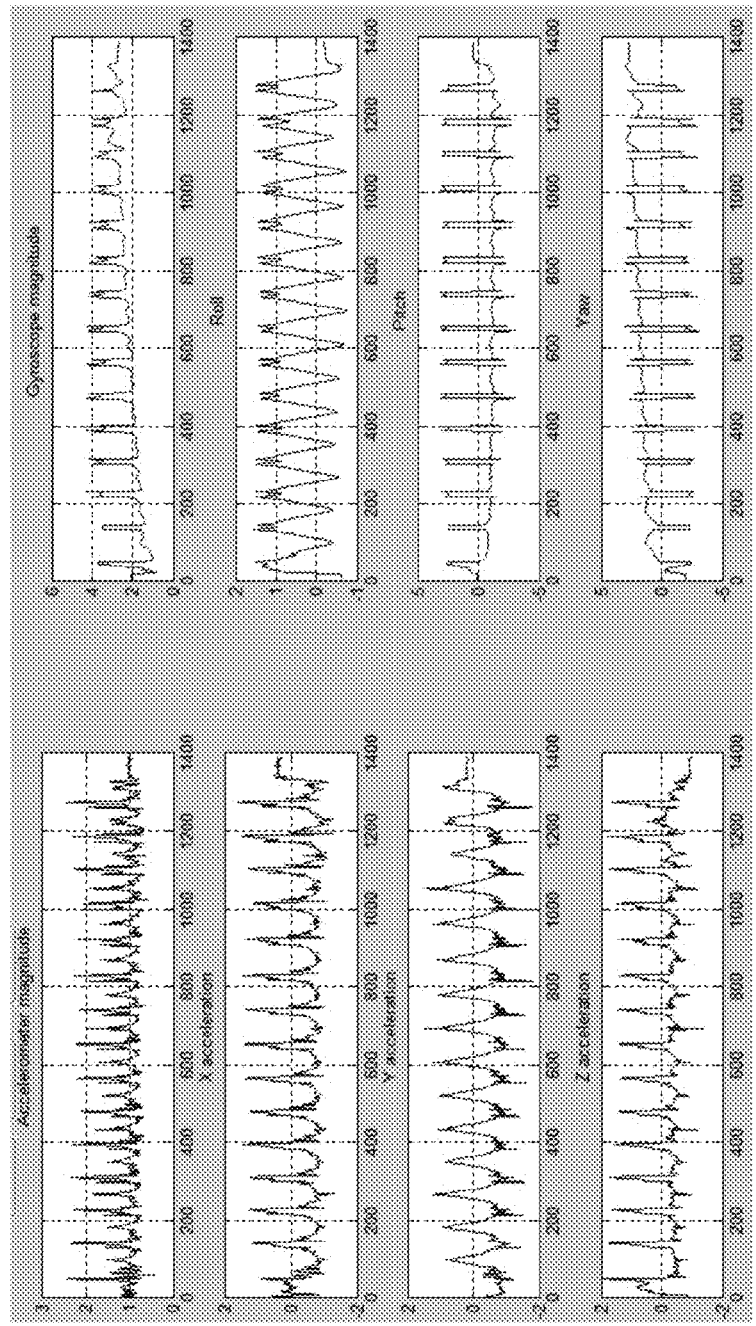
Figure 8:
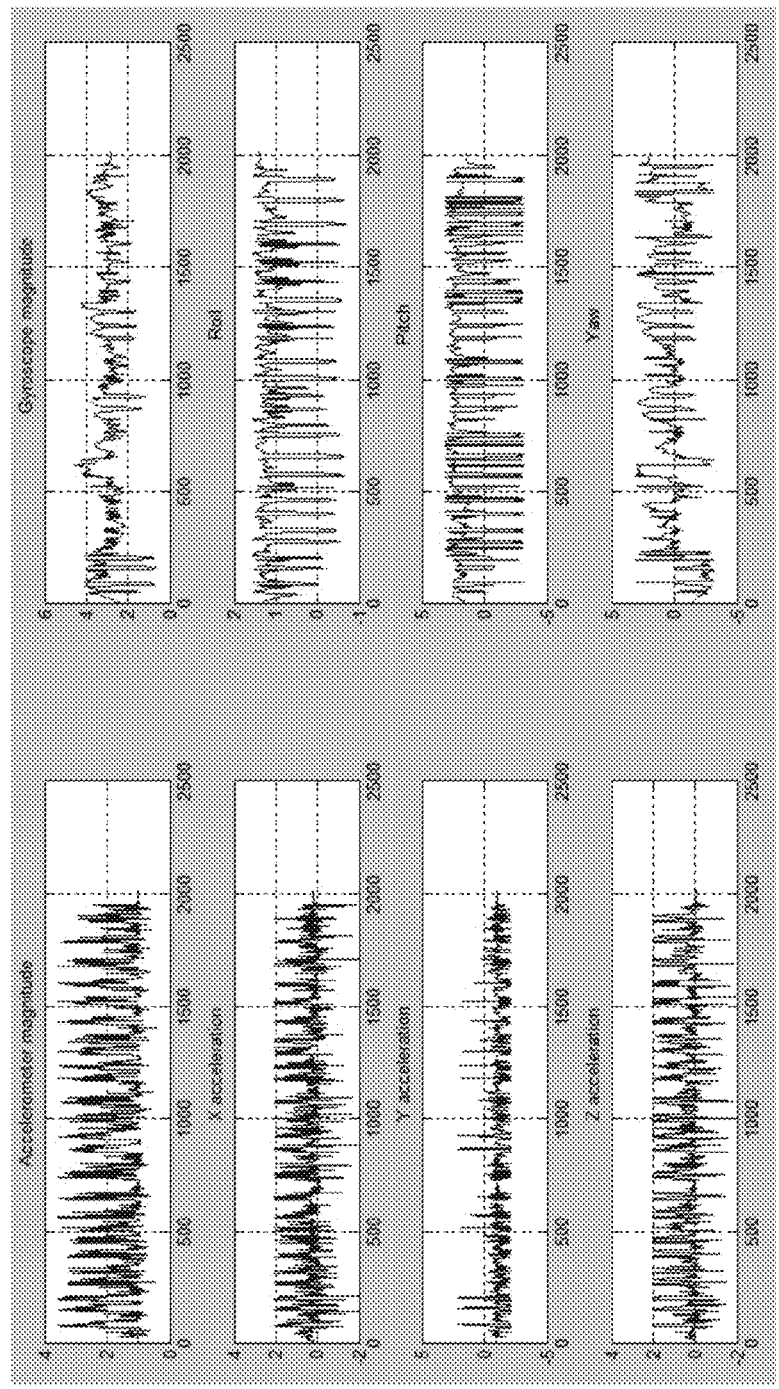
Figure 9:
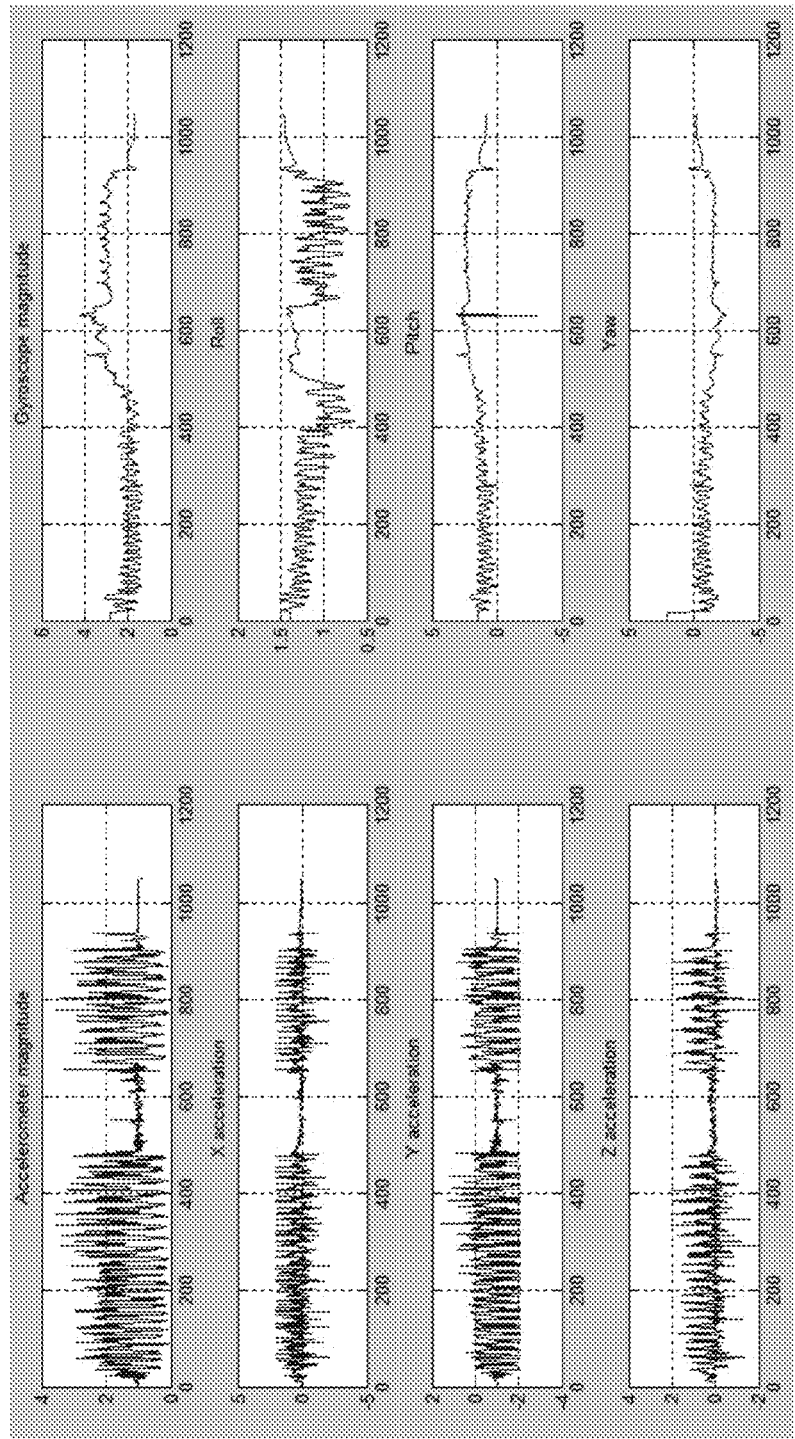
Figure 10:
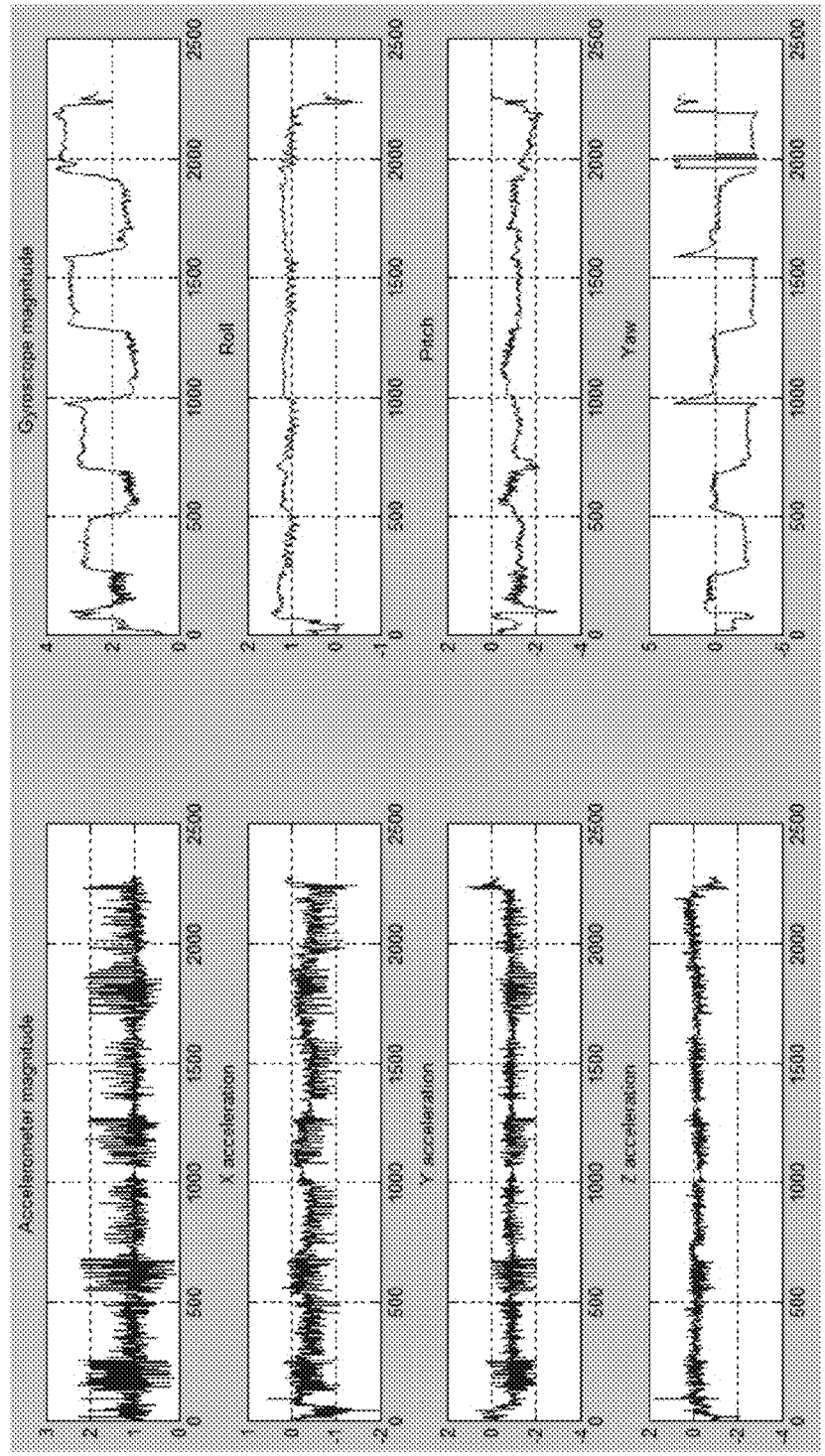
Figure 11:
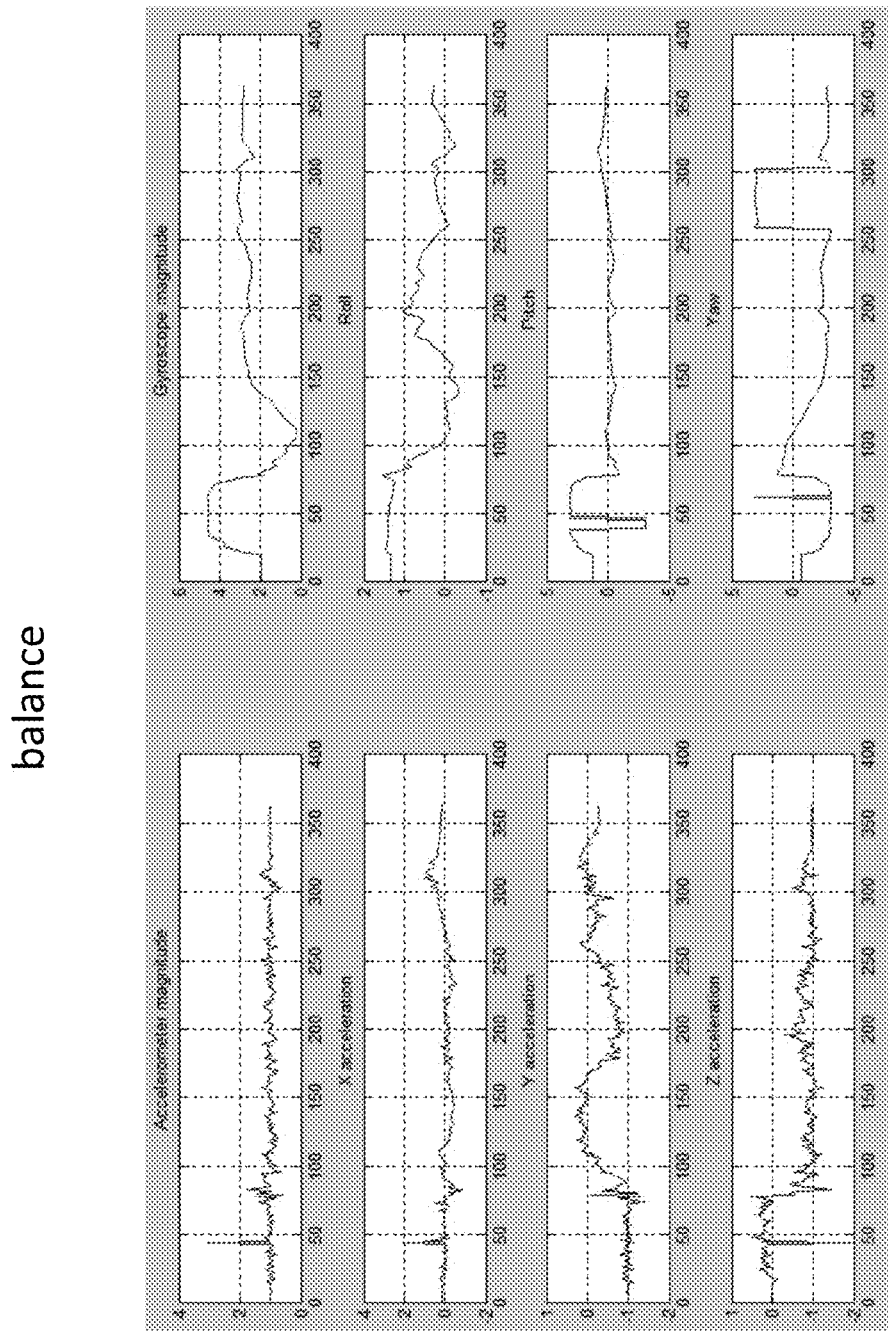

After the feature extraction, the frame classification module 232 performs activity classification for every frame. In an embodiment, the frame classification module uses an appropriate learning algorithm for the underlying good-feature distribution. For example, if feature distribution is Gaussian, the frame classification module can use a multivariate Gaussian classifier. On the other hand, the frame classification module can use a Bayesian neural network for multi-modal feature distribution. Since single-stage classification may not be optimal for decisions involving a large number of classes, the hierarchical classification module 234 performs hierarchical sequential pruning classification that groups similar classes based on feature distribution and then makes simpler classification decisions first, followed by more complex decisions hierarchically using optimized feature subsets at each stage of the classification decision process. FIG. 3 shows the frame-by-frame classification decisions for three major activity categories, such as walk/run, elliptical, and cycling, in accordance with an embodiment of the invention.

The activity clustering unit 212 and the event-based classification unit 214 leverage both time gap and sequential classification decisions to identify distinct physical activity events from which their parameters are to be estimated. Sequential decision looks for the most likely $P(C_{t+1}|C_t)$, where $C_t$ is the classification decision at time t. That is, when event-based clustering and classification are performed, the activity clustering and event-based classification units take advantage of the fact that people do not rotate activities from elliptical to cycling to running frequently. FIG. 3 shows both frame-based and event-based classification decisions for treadmill run, elliptical, stationary bike, and outside walk in accordance with an embodiment of the invention.

The event parameter extraction unit 216 processes each event segment looking for a number of parameters to characterize the event. Event parameters are optimized for each activity category. For example, parameters associated with a run event encompass start time, duration, total distance, total steps, overall speed, aerobic steps, run steps, run distance, run speed, run duration, high-intensity interval training (HIIT) flag, VO2 max (maximal oxygen uptake), burned calories, etc. For a cycling event, the event parameter extraction unit may compute total distance, average speed, route (if GPS information is available), start time, total duration, cycling duration, average rotations per minute (rpm), and burned calories. For stair climbing, parameters may include start time, duration, total steps, total climb steps, number of stairs, average climb steps per min, calories, etc. For interval motions, the event parameter extraction unit may estimate performance parameters, such as, but not limited to, count (for example, number of squats), range of motion, balance, strength/intensity, and speed. FIG. 3 shows examples of event parameters optimized for various activities in accordance with an embodiment of the invention.

The motion-sensing and motion-recognition algorithm of the sensor physical activity data processing engine is able to recognize a basis set of motions into which all human motions can be categorized due to skeleton-connective tissue structures of human anatomy. Listed below are examples of arm and leg motions the sensor physical activity data processing engine can capture as part of task-based health gaming.

1. Arm motions (measured with the sensing device, e.g., a sensor or a smartphone, attached to forearm)
   a. Abrupt, power moves used in boxing (upper cut, jab, cross, and hook)
   b. Smooth, rhythmic motions without weight as in yoga, stretching, Tai Chi, and swimming
   c. Similar motions as 2 during resistance training
   d. Typical body up/down motions during crunches, sit-ups, pushups, and chin-ups
2. Leg motions (ankle or pocket location for the sensing device)
   a. Abrupt, power moves used in martial arts kicks (side, reverse side, axe, butterfly, calf, crescent, hook, reverse roundhouse/heel, spinning back, flying, scissor, and vertical)
   b. Lots of little balancing movements on a balance board
   c. Jump motions
   d. Climbing stairs (pocket location for the sensing device)
   e. Squat (pocket location for the sensing device)
   f. Lunges
3. Full-body motions
   a. Overhead squat press
   b. Happy Body motions
   c. Tibetan monk rite motions
   d. Planks
   e. Tai Chi and Qi-Gong motions
   f. Relaxation, breathing motions FIGS. 4-11 show typical motion signatures captured through sensor signal processing and classification or recognition. In particular, FIGS. 4-11 show motion signatures for boxing, pushups, yoga, sit ups, kicks, jumping jacks, stair climb and balance, respectively.

Performance parameters estimated from these motions encompass the count of repetitive motions (pushups, jumping jacks, lunges, kicks, punches, etc.), range of motion (overhead squat press, Happy Body squats), wobbliness (balance and yoga motions), strength/intensity/explosiveness, and speed (explosive motions that require sudden burst). Positive user trial results on these motions have been described in "*Impacts of health data on predicting weight loss and engagement,*" by D. Kil, F. Shin, B. Piniewski, J. Hahn. and K. Chan, O'Reilly Strata Rx conference, San Francisco, October 2012, which is incorporated herein by reference.

Gaming tasks are designed to incorporate these motions in short sequences such that physical activities are fun and more efficient than just running or walking. For instance, these motions are designed to emphasize flexibility, balance, strength, and conditioning.

Figure 12:
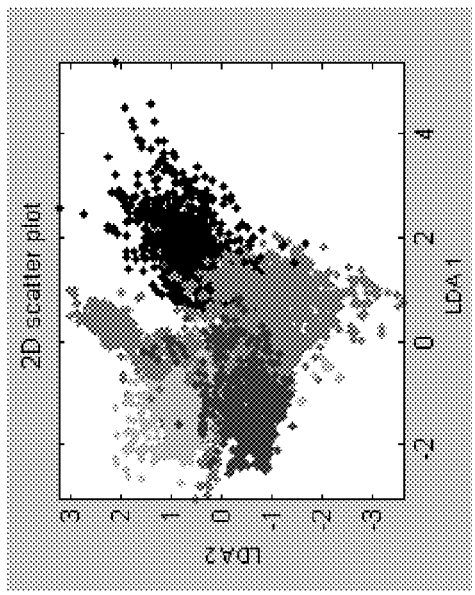
FIG. 12 shows feature scatter plots of eight distinct motions.
Figure 12:
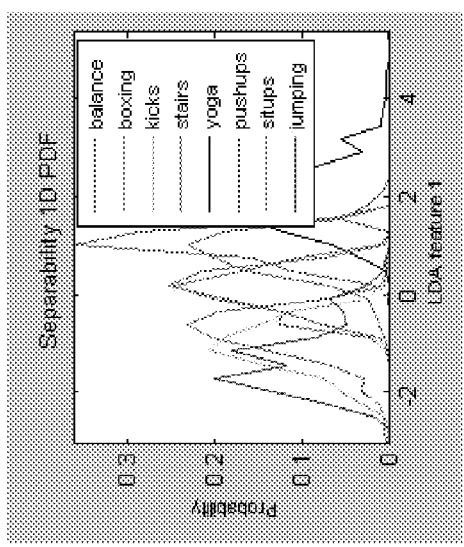
Figure 12:
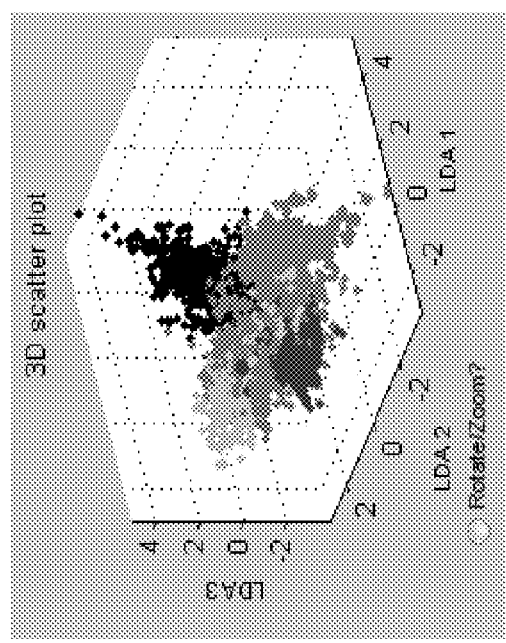

As part of gaming tasks, these motions will be optimized and personalized to each user. For instance, the task of performing X pushups in Y seconds can be tailored to the user's strength level since not only can the motion-sensing algorithm identify the motion type, but it can estimate the parameters of repetitive motions that exist in, for example, sit-ups, pushups, punches, kicks, and stair climbing. FIG. 12 shows feature scatter plots of eight distinct motions. As can be seen, there is enough class separation in the feature space to produce accurate frame-by-frame classification decisions with further performance improvement through event-based classification.

Motion classification algorithms are implemented as part of a multiple-motion classification or a two-class identification problem depending on how motion sensing is used in health gaming. For instance, a reminder-based or promptbased gaming task ("do 15 pushups in one minute") is inherently a two-class identification problem in that the classification algorithm computes how closely the user performed the reminded task. The degree of pattern matching can itself be a source of fun to the user as is commonly done in karaoke singing score feedback in karaoke bars.

Figure 13:
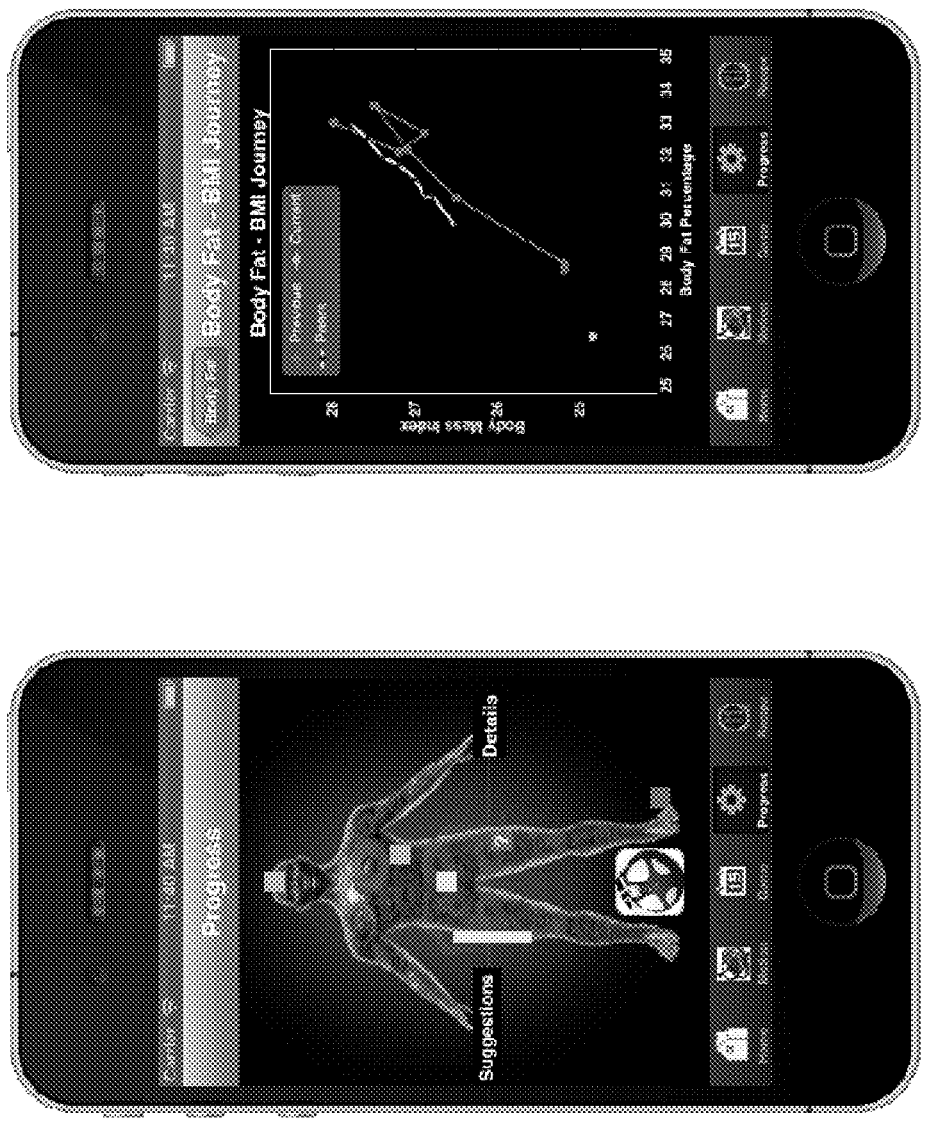
FIG. 13 shows a representative dashboard on a smartphone with brain fitness, cardio score, strength, flexibility, balance, and body composition in accordance with an embodiment of the invention.

When motion performance parameters are coupled with weight, body fat, heart rate, and game scores, the fitness gaming application can provide a comprehensive health dashboard with recommendations on how to improve health further. FIG. 13 shows a representative dashboard on a smartphone with brain fitness, cardio score, strength, flexibility, balance, and body composition (weight and body fat) in accordance with an embodiment of the invention. The progress dashboard shows user health status in the areas of brain (mind games), heart (cardio motions and subsequent heart-rate recovery), speed (foot), strength (core), flexibility (quadriceps), posture (long stick around the waist), and body composition (body fat and weight). The "?" on flexibility indicates that it is time for a flexibility test to see how much progress the user has made since the last test. Different colors may be used to represent fitness states. For example, red, yellow and green colors may be used to represent three fitness states. Other color schemes, such as martial arts belt colors, may be used in certain situations.

Figure 14:
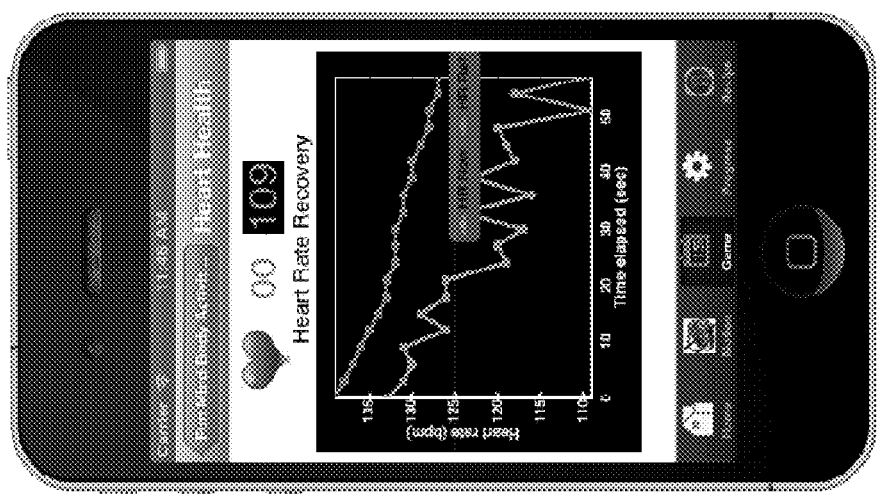
FIG. 14 shows the fitness game application measuring and tracking heart rate (HR) in terms of max HR and HR recovery in accordance with an embodiment of the invention.
Figure 14:
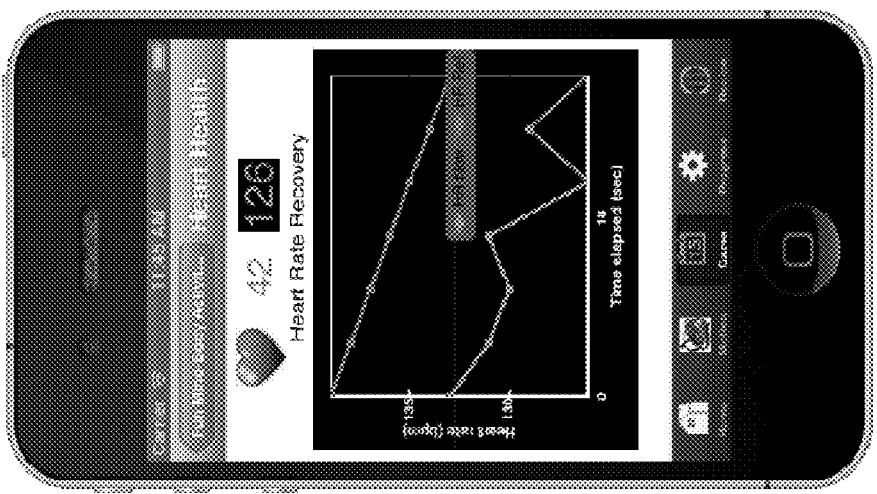

For those who do not want to use a motion sensor, the fitness game application may rely on the smartphone's camera sensor and flash to measure heart-rate recovery during a rest period by measuring the reflected light from the face of the user. For example, after the user performs three cardio motions, e.g., jumping jacks, jog in place, and burpees, the fitness game application asks the user to check the heart rate during 1-min rest. FIG. 14 shows the fitness game application measuring and tracking heart rate (HR) in terms of max HR and HR recovery in accordance with an embodiment of the invention. Similarly, the user can perform three flexibility, balance and meditation motions after which the user can measure the HR to see if it is dropping with more meditation. Furthermore, the fitness game application may show how much faster the user's HR recovers in comparison to the user's peers, as illustrated in FIG. 14.

The matchmaking engine, which performs the matchmaking operation at block 103 in FIG. 1, helps create a new, vibrant social network that fosters the fast adoption of healthy behaviors in a cost-effective, scalable way. It works as follows:
1. Expansion of the user's existing social network with opportunistic insertion of influencers for fast growth and deliberate insertion of role models and friends with high activity DNA compatibility, empathy, and success likelihood for fast diffusion of healthy behaviors.
2. Peer-to-peer nudging games with real-time feedback, tips, and recommendations based on linked-event pattern matching, where linked-event patterns represent opportune moments of engagement.
3. Calculation of social support scores to identify natural peer-to-peer coaches for whom coaching is intrinsically motivating and proven effective based on quantifiable outcomes.

Friends' activity social graph (FASG) embodies the aforementioned principles in order to harness the power of social network scalability in guiding people towards adopting healthier lifestyles. FASG perturbs and expands the user's existing social network by recommending change agents. It promotes friends encouraging friends during moments of high engagement based on real-time linked events. It nudges the user toward physical activities with real and virtual workout buddies in the ever-expanding FASG. It facilitates the transmission of positive reinforcements and encouragements between friends when significant events occur, such as new record VO2 max, winning a game, accomplishing a challenging goal, sudden negative changes in daily lifestyle, etc. FASG is used by the matchmaking engine to recommend real friends to the user of the fitness game application.

Figure 15:
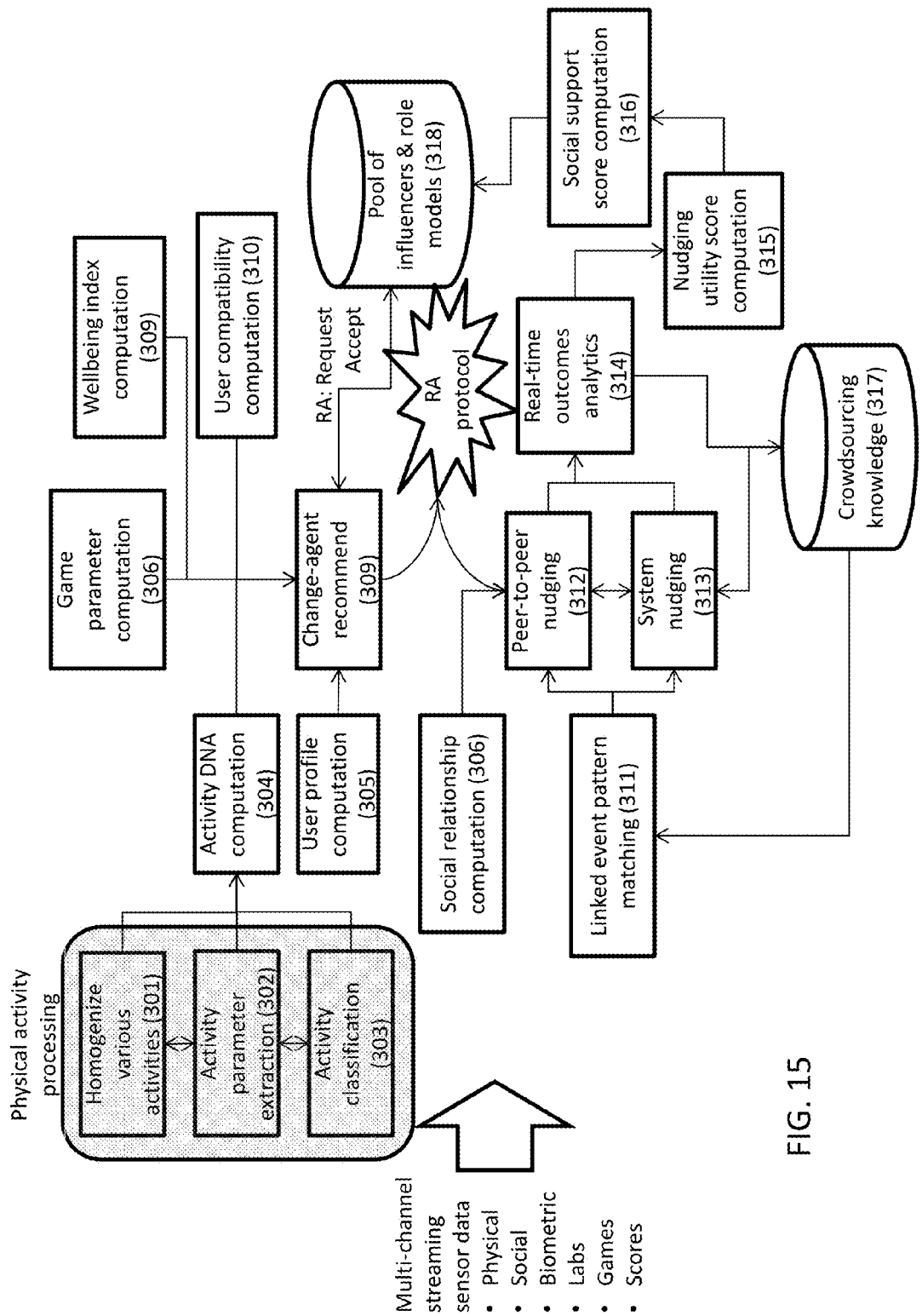
FIG. 15 is a processing block diagram for a matchmaking engine in accordance with an embodiment of the invention.

FIG. 15 shows the overall processing block diagram for the matchmaking engine in accordance with an embodiment of the invention. The FASG matchmaking engine performs the following tasks:
1. Activity DNA compatibility matching (304) from homogeneous physical activity motion clusters (301), estimated user-activity parameters (302), and physical activity motion classification (303) by linking user preferences in motions to motion-performance parameters. As used herein, activity DNA refers to unique characteristics of physical activities performed by a user.
2. Calculations of user-profile parameters (305), social game parameters (306), wellbeing components (307), and social compatibility (308) so that change agents (309) can be recommended.
3. Linked-event pattern matching (311) to identify opportune moments for engagement and nudging by leveraging peer-to-peer nudging (312) based on social relationship scores (310) or system nudging (313) using content developed by experts for various linked-event patterns.
4. Real-time outcomes analysis (314) to understand which nudges by whom are effective so that nudging-based intervention utility functions (315) and social support scores (316) can be updated for learning, which is stored in a global pool of crowdsourcing knowledge base (317) and influencers/role models (318).

Activity DNA Computation

For activity DNA computation, user's physical activity (PA) patterns are updated periodically using a moving average data, for example, weekly using four-week moving average data. The activity DNA addresses three key issues:
1. when do you work out?
2. what activities do your enjoy at what intensity?
3. for each activity, what are your workout patterns?

The physical activity processing engine captures automatically the answers to these questions. In an embodiment, the activity DNA is succinctly summarized in three dimensions as average-per-day statistics for each user in terms of weekdays and weekends/holidays as follows:
1. Preferred workout hours (PWH): workout-hour probability density function (PDF), workout hour vs. intensity joint PDF, workout hour vs. workout category joint PDF.
2. Preferred workout activities (PWA): workout-category PDF, workout category vs. intensity joint PDF.
3. Workout parameters (WP): duration, calories burned, intensity, average intensity, intensity-level PDF.

The PWH component of the activity DNA is a one-dimensional (1D) encoding of marginal and joint PDFs. For example, workout-hour probability PDFs is a 24×2 matrix of the fraction of equivalent steps during weekdays (Mon-Fri) and weekends (Sat-Sun, holidays). If the user exercises mostly in the morning while taking a walk after dinner during weekdays, the first column will have high numbers in morning hours and medium numbers in evenings, with very little in-between hours. The workout hour vs. intensity PDF is a 24×3 (intensity levels)×2 (weekday and weekend) array. Similarly, the workout hour vs. category PDF is a 24×$N_{cat}$×2 array, where $N_{cat}$ is the number of PA categories as determined by the accelerometer/gyroscope-based activity tracker. The PWH component is a $(24'2+24\times3\times2+24\times N_{cat}\times 2)$-by-1 vector. The PWA component is a 1D encoding of the two joint PDF matrices with the length of $N_{cat}\times2+N_{cat}\times3$. Finally, the WP component is a 1D array of workout parameters.

These PA patterns are collectively known as activity DNA, which is used to compute compatibility between different users. Activity DNA compatibility is measured in these three dimensions for maximum flexibility in workout buddy recommendation. For new users, their activity DNA can be initialized through questions and answers (Q & A) during registration, which is then updated as more sensor data becomes available.

Wellbeing Index Computation

The wellbeing components for the wellbeing index computation are divided into physical, social/emotional and medical. The user will have total control on which wellbeing components get displayed on FASG once the user opts in. The physical wellbeing score in absolute and relative metrics is based on the duration, total equivalent steps, total calories burned, intensity, and variety of workouts, with correlations between covariates taken into account. Furthermore, the predicted future PA level is included so that the score has some predictive power. The relative physical wellbeing score is measured against similar cohorts. The user can be assigned a default people-like-me (PLM) cohort group, which the user can refine. The social/emotional wellbeing score is comprised of the user's social network (SN) activity statistics, social support/influence in terms of spreading healthy lifestyle to friends in the network, improvements in friends' wellbeing indexes once they join the user's social network, and participation in service features. The SN activity statistics encompass the number of friends, the number of recent friends added, the level of communications, the number of shared objects, the number of postings/comments, and the network equivalency measure, i.e., PDF statistics of the user's social relationship strength.

The medical wellbeing score is based on a combination of disease burden and progression or trend, along with metabolic syndrome and insulin resistance approximated by biometrics and biomarkers. For example, insulin resistance can be approximated using the triglyceride-to-HDL ratio while the metabolic syndrome score is calculated based on waist circumference, body mass index (BMI), HDL-C, triglycerides, mean arterial pressure ((SBP–DBP)/3), and homeostasis model assessment, which is an indicator of insulin resistance calculated as fasting insulin (uU/mL)× fasting glucose (mg/dL)/22.5. The disease burden score (DBS) is a composite of all chronic conditions of the user. Based on actuarial data from the Centers for Medicare and Medicaid Services (CMS), the costs associated with each chronic disease alone and in combination with other chronic disease conditions are estimated. This forms the basis of the DBS. Associated with each chronic disease is a set of potential complications. For instance, diabetes can lead to neuropathy, retinopathy, microvascular issues that can result in foot amputation, end-stage renal disease that could require dialysis, erectile dysfunction, and stroke. The disease progression score (DPS) is an additive score based on P(Complications I Chronic disease). The role-based permission policy can allow the user's physician to monitor all his patients using a similar patients' activity social graph (PASG) and send real-time tips and recommendations to the patients showing changes that require immediate attention.

Game Parameter Computation

The gaming platform has collaboration, creation, challenge, and wagering games. Each game is characterized by its enjoyment index. The enjoyment index for a user is calculated based on the following components:
1. The more friends and role models in the game, the more enjoyable. Higher relationship strength is a bonus.
2. The higher the activity DNA match scores between the user and the players, the more enjoyable.
3. The higher the compatibility scores between the user and non-friend players, the more enjoyable.

The enjoyment index is the weighted sum of the normalized scores of the three components.

User-Profile Parameter and Compatibility Computation

Compatibilities between two people are computed using (1) psychosocial motivational profiles, (2) interests and hobbies, (3) disease conditions, and (4) future disease risk scores from predictive models. Instead of computing pairwise compatibility calculation, the concept of vector quantization (VQ) in the four vector subspaces for both computational efficiency and flexible, multidimensional compatibility measures is used. Each user is assigned up to four VQ clusters.

Change-Agent Recommendation

Change agents perturb the user's existing environment for the better. The change agents are friends, role models, influencers, and games. Role models for the user are selected carefully based on:
1. Their current wellbeing indexes must be above role-model qualifying thresholds.
2. Social support score based on the actual performance on helping friends change behavior and improve health outcomes.
3. Past similarities with the user in the areas of disease conditions, biometrics, and activity DNA.
4. Similarities in user parameters as measured in VQ indexes.
5. DOS such that shorter DOS is preferred.
6. Game enjoyment index.
7. Influencer parameters, such as the number of friends and followers and social support score.
8. History of past recommendations, accepts, and rejects.

A composite score is generated for each change agent. Depending on the user preference, change agents with top scores in the four categories will be recommended. Once the recommendations are made, the user can join the recommended games and send friends/role model/influencer requests to the recommended ones.

Social Relationship Computation

The social relationship strength between friends m and n, s(m,n), is a weighted measure of their communications through various channels, such as public feed/comments, Facebook friends lists, real-time nudging messages, etc. That is, $s(m, n)=\Sigma_i w_i c(m, n)$, where i is the ith communication channel. Direct communications through inbox would have higher weights than public feed-comment methods of communications. Other communication channels include real-time nudging through FASG, group forums, and sharing activities between friends, such as goals, competition wins, etc.

Linked Event Pattern Matching and Social Nudging

The linked event pattern matching (LEPM) algorithm looks for opportune moments for real-time engagement and feedback. Examples encompass winning a competition, accomplishing a challenging goal, being in a rut, sudden changes in daily activities, setting new records, etc. There are icons associated with these engagement pattern vectors.

In an embodiment, the user's friends can be shown in a spiraling circle with the closer (higher social relationship score) friends nearer. Next to each friend can be a color summary of the friend's current wellbeing status and recent trend. For an approved caretaker, the medical wellbeing icon can be shown. In this case, the caretaker's patients' status can be shown in a spiral fashion.

If the friend's linked events match stored patterns personalized to the user (opt-in model), a personalized message can remind the user gently to get in touch with the friend while providing guidelines on talking points. For instance, if Bill is a good friend of Janet and her workout trend is dropping significantly with less aerobic workout as determined by the linked-event pattern matching engine, the system will suggest to Bill that he send her a note of encouragement along with a proposal to play tennis since they both enjoy playing tennis. In certain cases, the system will send personalized messages directly bypassing the peer-to-peer nudging.

On the other hand, the user can contact any friends in the user's circle to suggest fun workout activities that they can do together while seeing progress and nudging one another continuously. Next to each friend, recommended friends based on their compatibility scores can be shown.

Outcomes Analysis, Social Support Score, and Utility Function

Associated with each real-time event for nudging is an outcomes event that can help the system evaluate the effectiveness of the nudge. Events encompass trend indicators and span multiple time frames to facilitate the creation of dynamical event rules, such as sudden change in workout patterns. Moreover, such event encoding allows the system to detect changes post-nudging. The magnitude of the changes can be compared to a threshold set according to statistical hypothesis testing and desired p-value.

Each nudging is judged based on how successful it was to produce a desired outcome. Instead of using a binary number based on a threshold, the system uses the actual magnitude of change. Let n(t,u,f,e) denote a nudge delivered from friend f to user u at time t for a linked event e(t, t−1, . . . , t−N), where N is the time span of linked events. Let m(t:t+M,u,f,e) represent the magnitude of desired changes for user u and linked event e, post-nudge delivered by f and measured between time t and t+M. The utility score U for nudge n and friend f for linked event e delivered at time t is calculated as follows:

$$U(n(f, e)) = \frac{1}{L(\Psi)} \sum_{u \in \Psi}^{L} m(u, f, e),$$

where $\Psi$ and $L(\Psi)$ represent the user segment that the friend f has been able to nudge and the number of users touched by friend f included in ensemble averaging in computing U. In a nutshell, utility is the average effectiveness of a nudge applied to an appropriate population segment $\Psi$ for a particular linked event e by friend f The social support score is in part based on U(n(f,e)) in that the more impact the friend f has on the nudged users, the higher the score. The marginal utility can be summed over f and/or e to find natural peer-to-peer coaches/role models and linked events that are particularly engaging to the user from an outcomes perspective.

Figure 16:
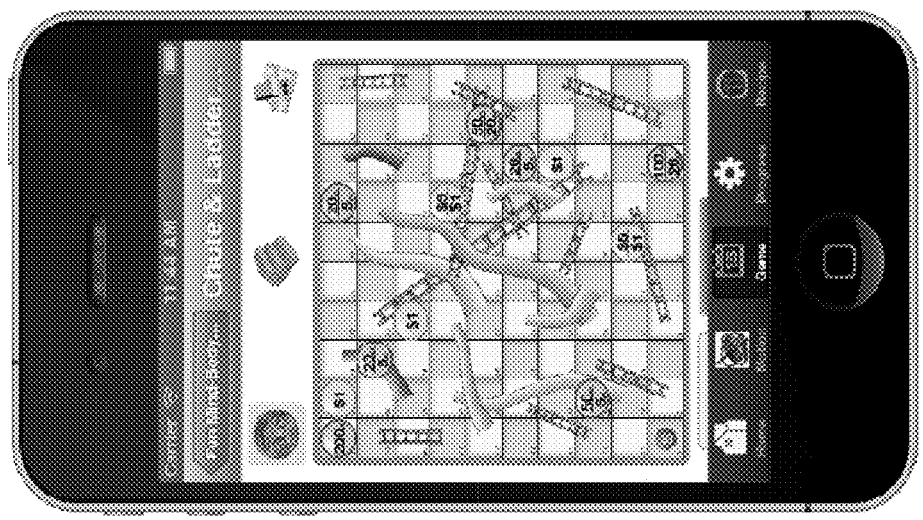
FIG. 16 shows the main game page of the fitness game application, where the user can play various mind-body and reward-based board games, in accordance with an embodiment of the invention.
Figure 16:
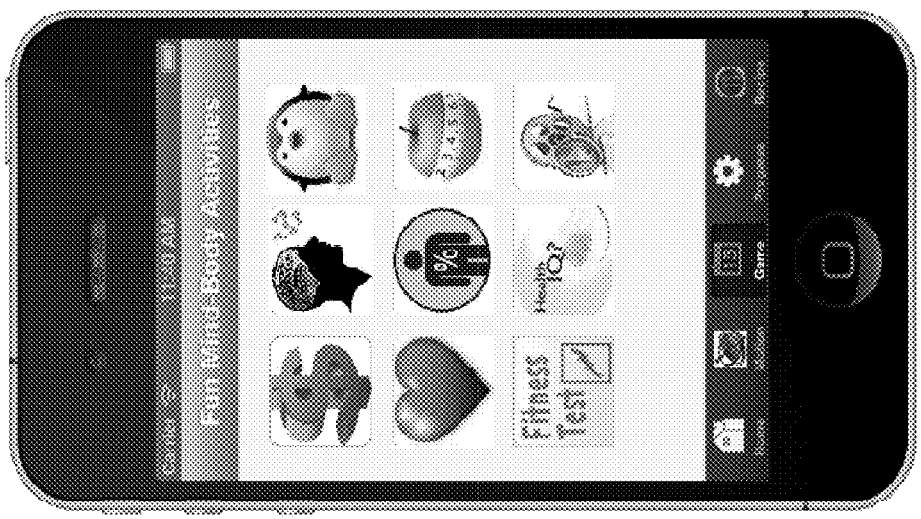

Turning now to FIG. 16, the main game page of the fitness game application is shown, where the user can play various mind-body and reward-based board games, in accordance with an embodiment of the invention. These games are recommended using collaborative filtering and the user's health states. The user may accumulate points by doing prescribed motions and spend the points on these games for enhanced benefits.

A game that can be provided in the fitness game application is color-in-motion (CIM) game, which is a game designed to bring out an inner artist in everyone. It is relaxing and rewarding to go out to a beautiful place and paint masterpiece that evokes passion. Furthermore, many enjoy outdoor photography. The game combines these hobbies and hidden desires. The CIM game utilizes a photograph or picture supplied by the user or in an image database as base image. A set of image processing and morphology algorithms prepares the image for painting as follows:
1. Filtering to remove unnecessary background, such as, but not restricted to, all-white background around the picture frame, too much salt-and-pepper noise unpleasing to the eyes, etc.
2. Adaptive image thresholding to identify different regions based on neighboring-pixel homogeneity: Thresholds are determined adaptively based on RGB (Red-Green-Blue) distributions of the image such that color and intensity details are accentuated.
3. Edge detection within each thresholded region.
4. Region-of-interest (ROI) detection using edges and morphology filtering.
5. ROI-boundary detection.
6. Fusion of ROI boundaries from different thresholds in black-and-white and RGB color.
7. Polygon representation of each ROI.
8. Threshold re-adjustment based on the number of polygons to control the level of details shown on canvas.
9. Special-effect image operators available for each polygon.

Figure 17:
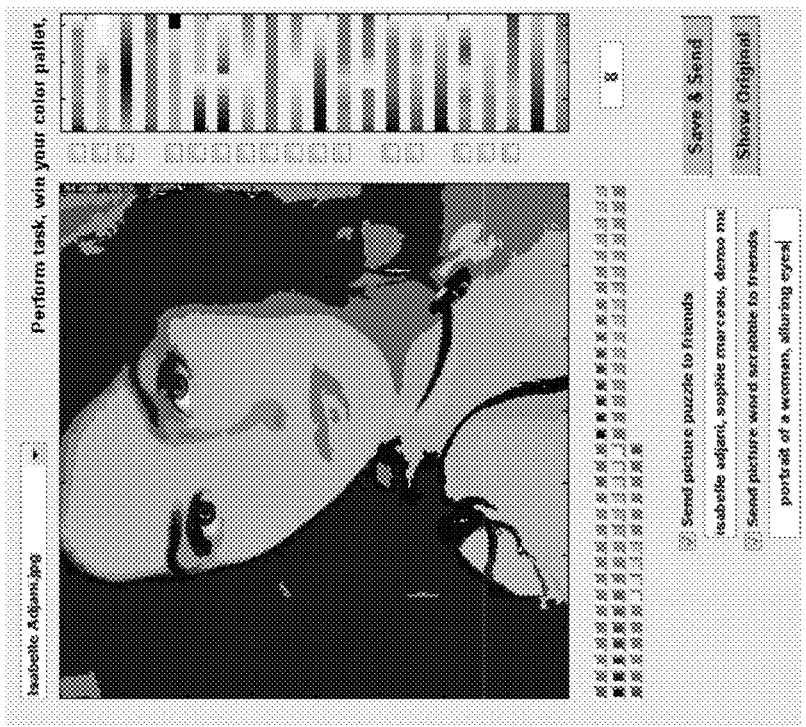
FIG. 17 shows a color-in-motion (CIM) game in accordance with an embodiment of the invention.
Figure 17:
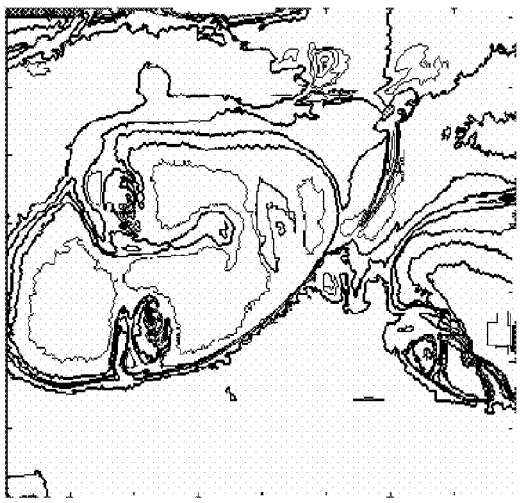

To play the CIM game, the user obtains a unique color map by performing a motion assigned to the color map. As the user feels the need for more color maps during painting, the user performs more tasks to obtain the right color maps from the list of color maps, as illustrated in FIG. 17, which shows the CIM game in accordance with an embodiment of the invention. The player adds the new color maps to his color palette and paints the canvas.

Additional items that can be obtained through motions include special-effect image processing operators, such as gradient, texture, smoothing, high-pass filtering, and random color mixture within a family of colors used in abstract painting. This game appeals to anyone who has dreamed of becoming an artist creating a masterpiece painting. The painting can be submitted to the crowdsourcing community, where other players can view and rate it. The average rating can be the basis by which the user gets more feedback on his or her creation. When others use the painting for other games, then the user may get royalty points, which can be a measure of the user's popularity and influence in the gaming social network.

Figure 18:
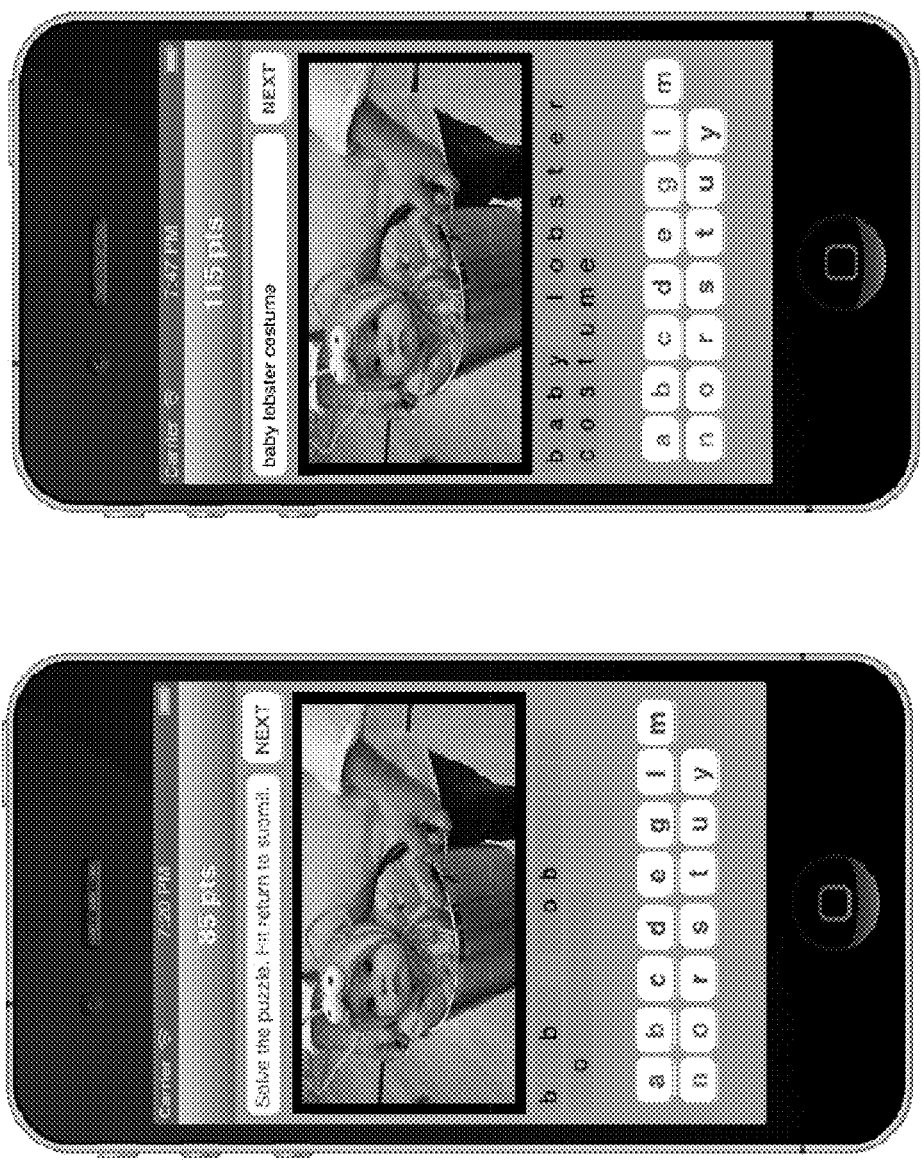
FIG. 18 shows a picture-word shuffle (PWS) game in accordance with an embodiment of the invention.

Another game that can be provided in the fitness game application is a picture-word shuffle (PWS) game, which combines picture, word shuffle, and word puzzle into one. In this game, the user can upload a picture and supply a title or first impression of the picture. The user can then send the picture to the user's friends. The game-creation engine embeds a fixed number of false letters to the mix depending on the degree of difficulty, assigns appropriate motions to the letters that include true (used) and false (unused) letters, and sends the game page to the specified friends. The player's fitness progress along with game points can become a basis for showcasing accomplishments and getting positive reinforcement from the crowd. FIG. 18 shows the PWS game in accordance with an embodiment of the invention in progress.

Another game that can be provided in the fitness game application is a word puzzle game. In this game, the user sends a phrase along with hints and a motion set appropriate for the recipient (outdoor or office or seated while watching TV, easy/medium/advanced). The phrase can be how he feels at the moment or something interesting that he just thought of. The game engine then takes care of the rest, setting up the board, populating the board with motions from the appropriate motion set, and sending the game board to the recipient with a push or email notification. If the game is sent to multiple recipients, they can collaborate or compete by taking turns and solving the puzzle. The recipient can then open the game board and can take a few actions. These actions include:
1. Use the provided chips to buy a letter that is in the phrase.
2. Go to the preferred letter, click on it, and perform the assigned motion. The user can earn points each time the user performs the motion.
3. Use the points to buy a clue. The clue can be in the form of showing two letters, one of which is in the phrase.

Figure 19:
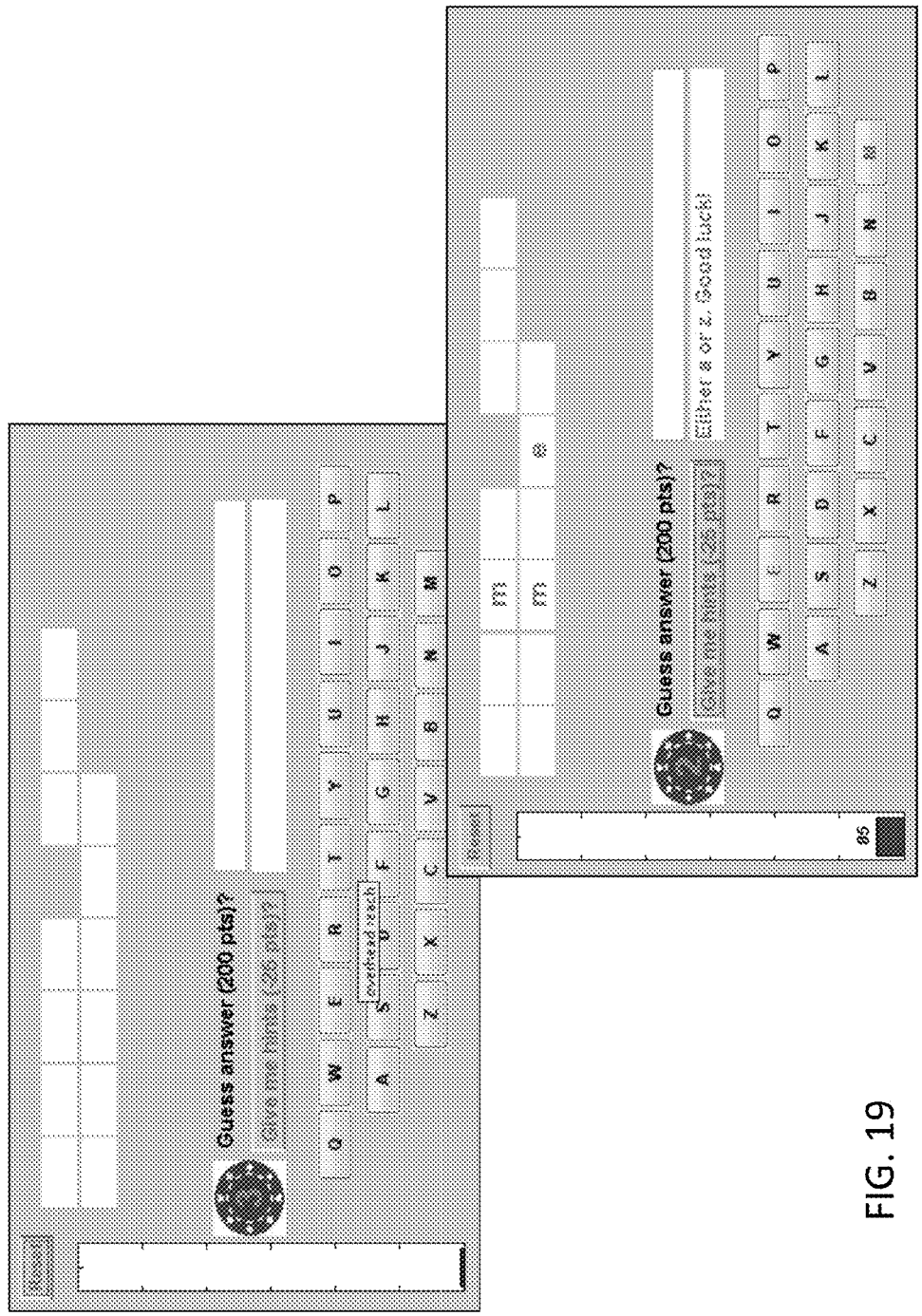
FIG. 19 shows a word puzzle game in accordance with an embodiment of the invention before and during the play.

When the user has enough clues, the user can solve the word puzzle or keep performing more motions for points. Parents or grandparents can configure the game such that when kids earn certain points, they can receive pledged prizes of mystery for more fun. FIG. 19 shows the game board of the word puzzle game in accordance with an embodiment of the invention before and during the play.

Figure 20:
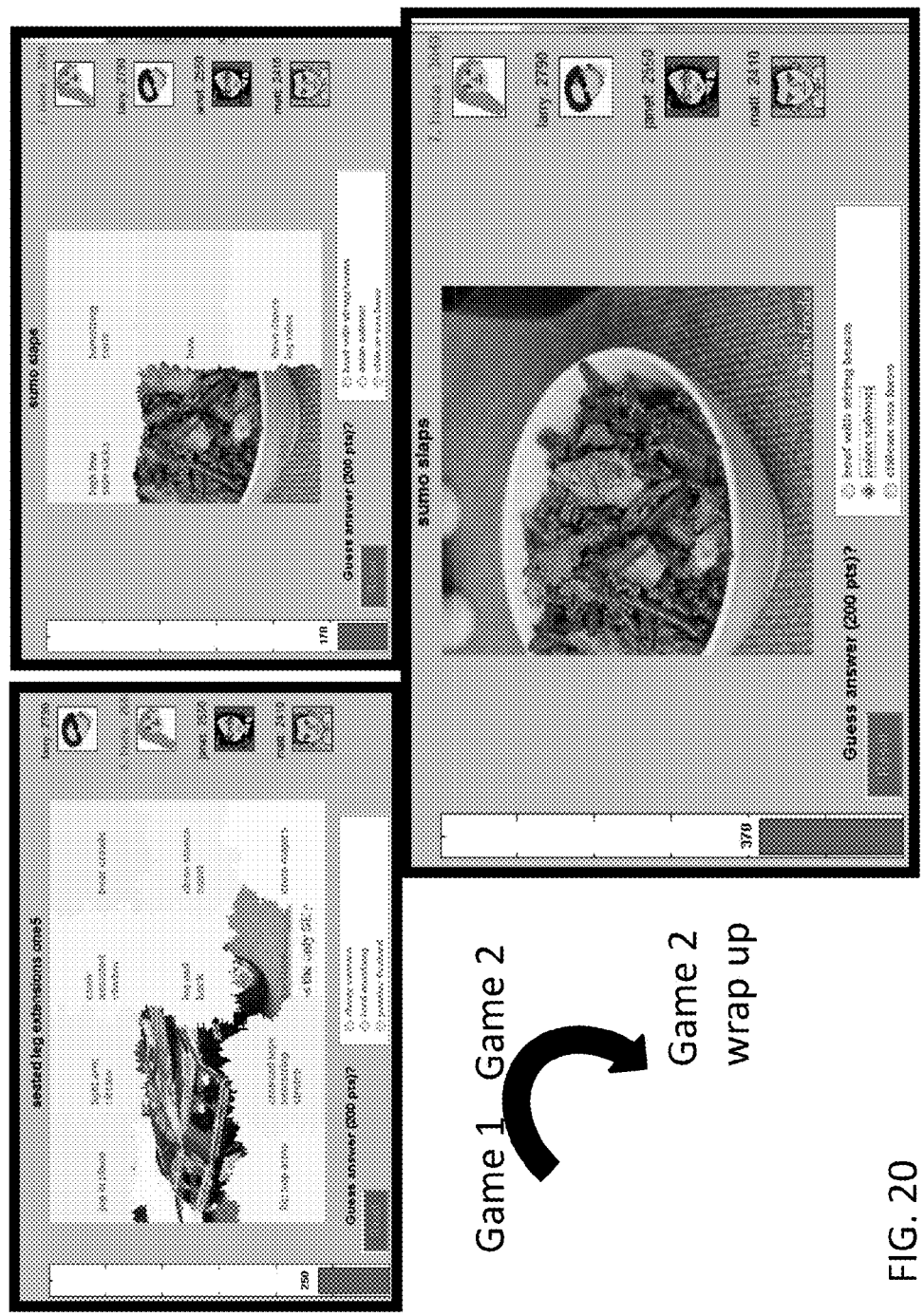
FIG. 20 shows the game screen for a picture jigsaw game before and during the play in accordance with an embodiment of the invention.

Another game that can be provided in the fitness game application is a picture jigsaw game. In this game, the user uploads a picture, provides multiple choices with a correct answer, and a motion set appropriate for the recipient's health status and environment. The recipient sees the game image, which is initially covered with motions to perform. As the recipient performs a specified motion one by one, each jigsaw piece of the picture is revealed. At any time, the recipient can guess the answer to the jigsaw puzzle. FIG. 20 shows the game screen for the picture jigsaw game before and during the play in accordance with an embodiment of the invention. As can be seen, this game can be used as a way to communicate with friends and family members during travel to express the user's care about their wellbeing. If the user is in an exercise mood, he can browse various picture-puzzle categories, select a hidden picture, and start playing.

The crowdsourcing elements encompass, but not restricted to, game points, fitness progress, specific motions associated with improving certain fitness metrics, etc. Players can also compete based on the speed of solving the same picture jigsaw with the fastest player owning the picture and having his name associated with it.

Figure 21:
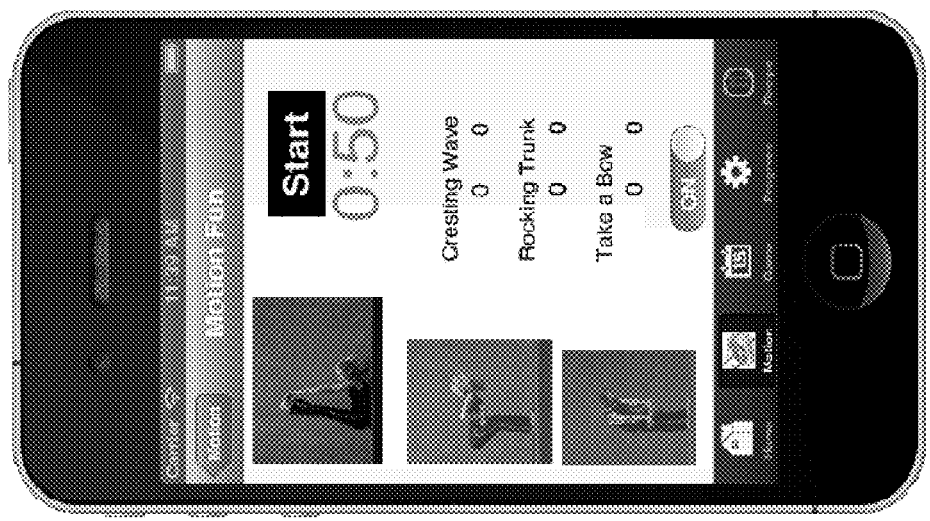
FIG. 21 shows a screenshot of a motion playlist in accordance with an embodiment of the invention.
Figure 21:
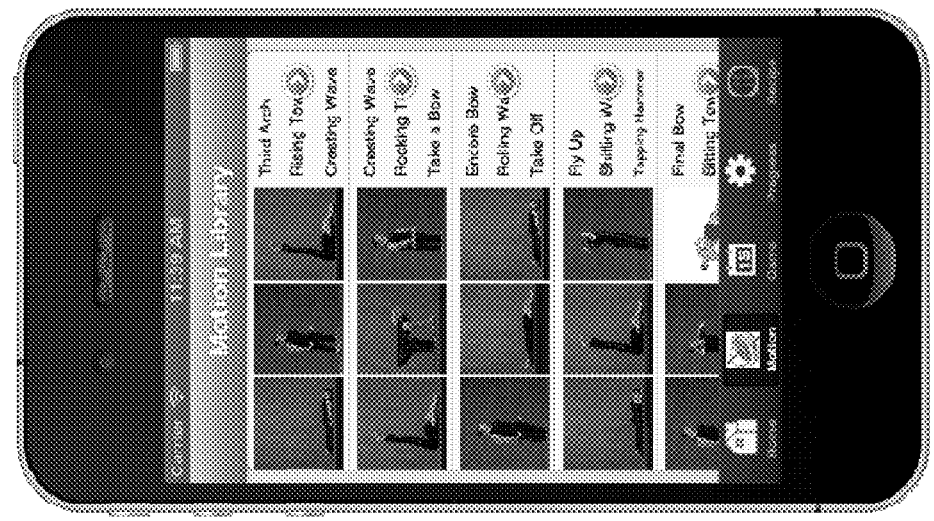

FIG. 21 shows a screenshot of a motion playlist in accordance with an embodiment of the invention, where these motions are either recommended or user favorites. The motions are categorized in terms of difficulty level, instruction level (easy to follow?), motion type (yoga, balance, strength, cardio, Happy Body, kata, Tai Chi, Qi-Gong, flexibility, gentle, etc.), body muscle groups, environment, and sensor location. In an embodiment, the motion home page where the user's favorite and recommended motions are presented in sets of three motions. When the user selects a 3-motion set, the timer with voice guides the user through the set. A typical sequence is 0.5- to 1-min motion followed by 15-sec rest during which the user sees motion score and performance parameter. The detailed motion page shows an animated gif or video so that the user knows exactly how to perform each motion.

Figure 22:
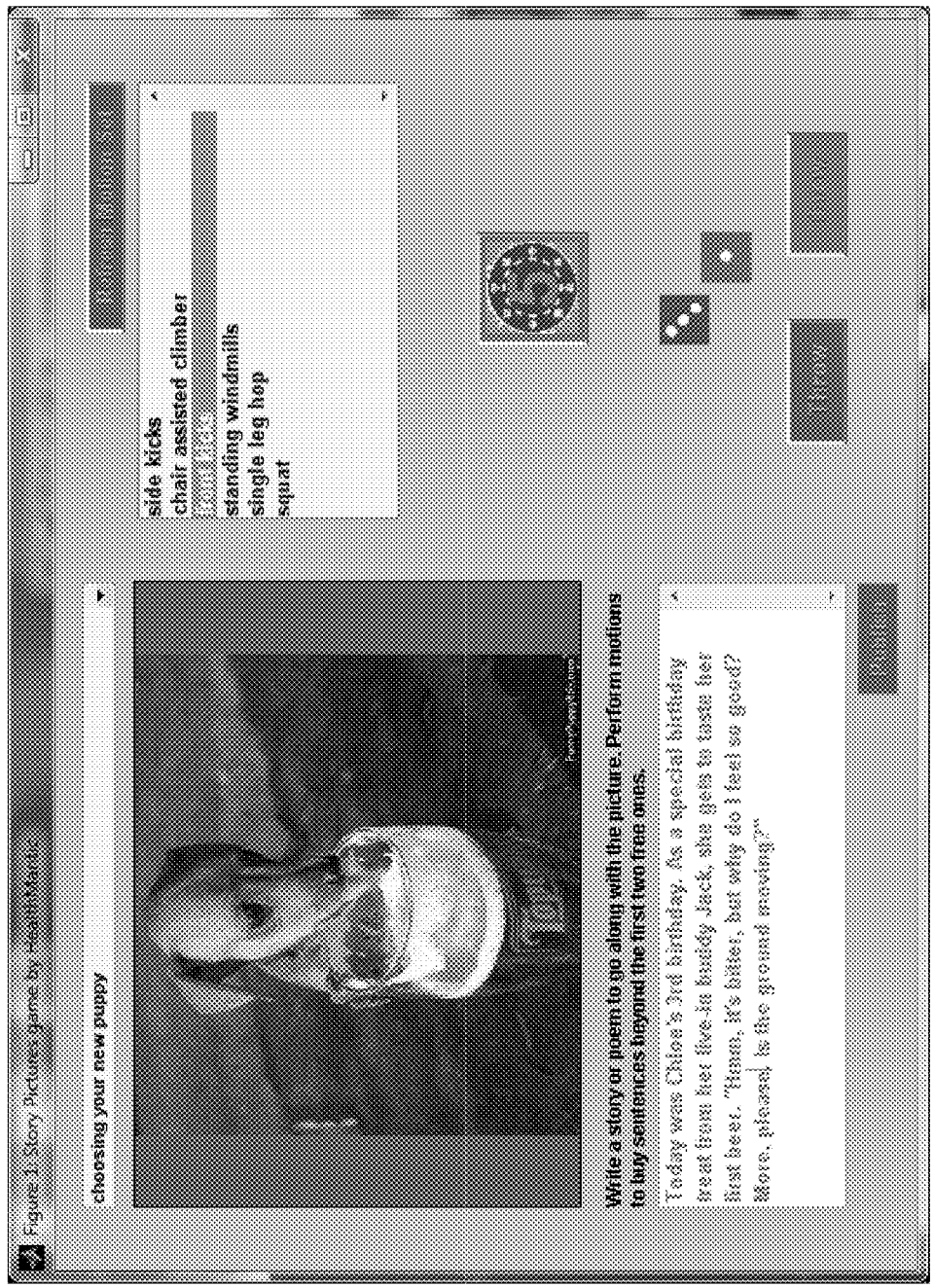
FIG. 22 shows the story picture in motion game in accordance with an embodiment of the invention

Another game that can be provided in the fitness game application is a story picture in motion game. This game couples short-duration motions with creative writing inspired by a picture. The story picture in motion game will be described using an example, as illustrated in FIG. 22, which shows the story picture in motion game in accordance with an embodiment of the invention. The user, Jack, takes a picture of his dog Chloe. He then sends a picture to his friend, Jane, for the story picture in motion game. The system then populates the game page for Jane. As shown in FIG. 22, she sees Jack's dog drinking beer. Jane starts with N free sentences. Then she is prompted to perform any of the six motions that Jack specified or the system selected based on Jack's gaming specifications. Every time she performs a task, she gains a new sentence with which to write a story about Jack's picture.

Jane rolls a dice to get a number. She then performs a motion that corresponds to her dice number, after which she gains another sentence. Her literary agent then throws the second dice. If the agent's dice number is below Jane's first throw, Jane wins an additional sentence. Furthermore, one of the six motions has a wild card, such that when Jane performs the wild-card motion, she wins more sentences.

After Jane accumulates enough sentences, she can start writing a story about the picture. After she finishes her story, she publishes it, which then goes back to Jack and the community for crowdsourcing. People can then see the picture and stories around the picture. They can vote or rate on the stories, which can be a basis for crowdsourcing-based leader boards, game royalty points, literary awards, etc. Jane can do the same on any image in an image database. She can search for inspiring images on the database, write a story about any of them, and then publish for crowdsourcing feedback. In short, the story picture in motion game combines the elements of exercise and creative writing with crowdsourcing components to give extra motivation to players.

Figure 23:
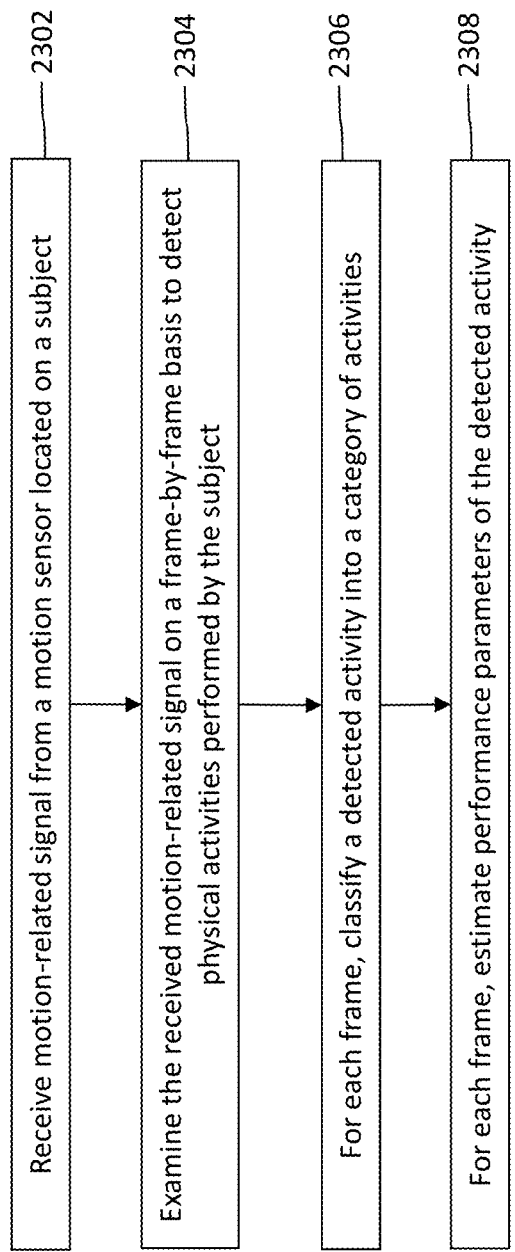
FIG. 23 is a process flow diagram of a method for processing motion-related sensor data for health application in accordance with an embodiment of the invention.

A method for processing motion-related sensor data for health application in accordance with an embodiment of the invention is described with reference to a process flow diagram of FIG. 23. At block 2302, motion-related signal from a motion sensor located on a subject is received. At block 2304, the received motion-related signal is examined on a frame-by-frame basis to detect physical activities performed by the subject. Each frame of the received motion-related signal represents a predefined time interval. At block 2306, for each frame, a detected activity is classified into a category of activities. At block 2308, for each frame, performance parameters of the detected activity are estimated.

Figure 24:
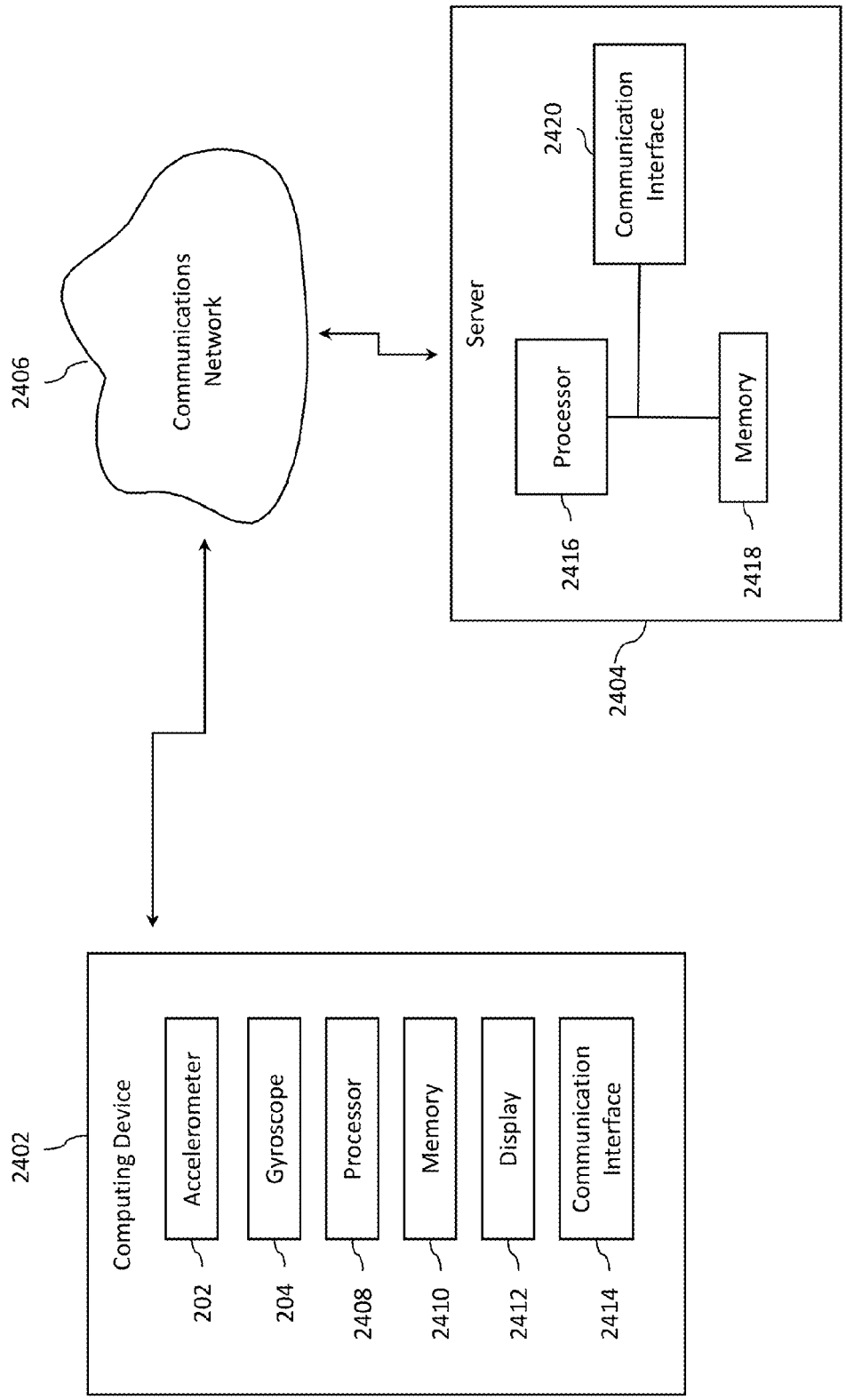
FIG. 24 is a block diagram of a fitness game system in accordance with an embodiment of the invention.

Turning now to FIG. 24, a fitness game system in accordance with an embodiment of the invention is shown. The fitness game system includes a computing device 2402 and at least one server 2404 that can communicate with the computing device via a communications network 2406. In the illustrated embodiment, the computing device includes two motion sensors, i.e., the accelerometer 202 and the gyroscope 204. However, one or more motion sensors may be external to the computing device and connected to the computing device via a wireless connection, e.g., Bluetooth, or a wire connection. The computing device further includes a processor 2408, memory 2410, a display 2412 and a communication interface 2414 to connect to the communications network, which may include the Internet. In an embodiment, the computing device is a smartphone. However, the computing device can be any type of a computer, such as a tablet, a personal computer or any computing device with a display screen and a processor, e.g., a central processing unit (CPU). In an embodiment, the fitness game application as described herein runs on the computing device. The server 2404 includes a processor 2416, memory 2418 and a communication interface to connect to the communications network 2406. Any additional servers would be similar to the server 2404.

The various processing modules and processing engines described herein may reside in the computing device 2302 and/or the server 2304. As an example, the digital signal processing unit 206 (shown in FIG. 2) may reside in the computing device, while other modules and engines reside in the server. In an embodiment, the processing modules and processing engines described herein are software programs running on the computing device and/or the server(s).

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods may be implemented using software instructions stored on a computer useable storage medium for execution by a computer. As an example, an embodiment of a computer program product includes a computer useable storage medium to store a computer readable program that, when executed on a computer, causes the computer to perform operations, as described herein.

Furthermore, embodiments of at least portions of the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The computer-useable or computer-readable medium can be an electronic, magnetic, optical, electromagnetic, infrared, or semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disc, and an optical disc. Current examples of optical discs include a compact disc with read only memory (CD-ROM), a compact disc with read/write (CD-R/W), a digital video disc (DVD), and a Blue-ray disc.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for processing motion-related sensor data for health application, the method comprising:
   receiving motion-related signals from motion sensors located on different subjects, wherein the motion sensors comprise at least one accelerometer and at least one gyroscope integrated within a smartphone;
   processing the received motion-related signals on a frame-by-frame basis to detect distinct short-duration exercise motions performed by the subjects, the distinct short-duration exercise motions including arm motions, leg motions and full body motions, each frame representing a predefined time interval shorter than the total duration of a distinct short-duration exercise motion;
   for each frame, performing a plurality of signal transformations to extract features for activity classification;
   for each frame, performing hierarchical decision making using feature subsets for a plurality of different categories of short-duration exercise motions to classify a number of motion categories of the plurality of different categories of short-duration exercise motions;
   for each frame, classifying a detected distinct short-duration exercise motion into one of the number of motion categories;
   for each frame, estimating performance parameters of the detected distinct short-duration exercise motion, wherein the performance parameters define the performance of the detected distinct short-duration exercise motion in the frame; and
   creating a picture-based mind-body and reward-based game that is associated to a particular subject of the different subjects, wherein the picture-based mind-body and reward-based game includes at least one of the distinct short-duration exercise motions to be performed using the smartphone to play the picture-based mind-body and reward-based game.

2. The method of claim 1, wherein the classifying includes classifying the detected distinct short-duration exercise motion into one of the different categories of distinct short-duration exercise motions using a learning algorithm.

3. The method of claim 1, wherein the estimating includes estimating the performance parameters of the detected distinct short-duration exercise motion using a bank of matched filters.

4. The method of claim 1, wherein the estimating the performance parameters of the detected distinct short-duration exercise motion includes estimating at least one of counts for each frame, range of motion for each frame, balance score for each frame, steps/strides per frame and revolution per frame.

5. The method of claim 1, wherein the received motion-related signals are from smartphones.

6. The method of claim 1, further comprising transmitting the picture-based mind-body and reward-based game to one or more recipients associated with the particular subject so that the picture-based mind-body and reward-based game can be played by at least one of the recipients.

7. The method of claim 6, further comprising matching the particular subject to at least one of the recipients based on at least one of activity compatibility, wellbeing index, playing patterns, user profile and social relationship of the subject and the recipients.

8. The method of claim 1, further comprising submitting results of the picture-based mind-body and reward-based game to a crowdsourcing community for feedback.

9. The method of claim 1, further comprising recommending the picture-based mind-body and reward-based game to the particular subject, wherein the picture-based mind-body and reward-based game involves using points to play, and wherein the points are accumulated by performing at least one of the distinct short-duration exercise motions.

10. A system for processing motion-related sensor data for health application, the system comprising:
computer memory;
processor configured to:
receive motion-related signals from motion sensors located on different subjects and to process the received motion-related signals on a frame-by-frame basis to detect distinct short-duration exercise motions performed by the subjects, the distinct short-duration exercise motions including arm motions, leg motions and full body motions, each frame representing a predefined time interval shorter than the total duration of a distinct short-duration exercise motion, wherein the motion sensors comprise at least one accelerometer and at least one gyroscope integrated within a smartphone;
perform, for each frame, a plurality of signal transformations to extract features for activity classification;
perform, for each frame, hierarchical decision making using feature subsets for a plurality of different categories of short-duration exercise motions to classify a number of motion categories of the plurality of different categories of short-duration exercise motions;
classify, for each frame, a detected distinct short-duration exercise motion into one of the number of motion categories;
estimate, for each frame, performance parameters of the detected distinct short-duration exercise motion, wherein the performance parameters define the performance of the detected distinct short-duration exercise motion in the frame; and
create a picture-based mind-body and reward-based game that is associated to a particular subject of the different subjects, wherein the picture-based mind-body and reward-based game includes at least one of the distinct short-duration exercise motions to be performed using the smartphone to play the picture-based mind-body and reward-based game.

11. The system of claim 10, wherein the processor is configured to classify the detected distinct short-duration exercise motion into one of the different categories of distinct short-duration exercise motions using a learning algorithm.

12. The system of claim 10, wherein the processor is configured to estimate the performance parameters of the detected distinct short-duration exercise motion using a bank of matched filters.

13. The system of claim 10, wherein the processor is configured to estimate at least one of counts for each frame, range of motion for each frame, balance score for each frame, steps/strides per frame and revolution per frame.

14. The system of claim 10, wherein the received motion-related signals are from smartphones.

15. The system of claim 10, wherein the processor is configured to transmit the picture-based mind-body and reward-based game to one or more recipients associated with the particular subject so that the picture-based mind-body and reward-based game can be played by at least one of the recipients.

16. The system of claim 15, wherein the processor is further configured to match the particular subject to at least one of the recipients based on at least one of activity compatibility, wellbeing index, playing patterns, user profile and social relationship of the subject and the recipients.

17. The system of claim 10, wherein the processor is configured to submit results of the picture-based mind-body and reward-based game to a crowdsourcing community for feedback.

18. The system of claim 10, wherein the processor is further configured to recommend the picture-based mind-body and reward-based game to the particular subject, wherein the picture-based mind-body and reward-based game involves using points to play, and wherein the points are accumulated by performing at least one of the distinct short-duration exercise motions.

* * * * *